US011033338B2

(12) United States Patent
Sugie et al.

(10) Patent No.: US 11,033,338 B2
(45) Date of Patent: Jun. 15, 2021

(54) MEDICAL INFORMATION PROCESSING APPARATUS, INFORMATION PROCESSING METHOD, AND MEDICAL INFORMATION PROCESSING SYSTEM

(71) Applicant: SONY CORPORATION, Tokyo (JP)

(72) Inventors: Yuki Sugie, Kanagawa (JP); Daisuke Kikuchi, Kanagawa (JP); Tomoyuki Hirayama, Kanagawa (JP); Yasuhiro Matsuda, Tokyo (JP); Daisuke Nagao, Kanagawa (JP); Takara Kasai, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 303 days.

(21) Appl. No.: 16/070,317

(22) PCT Filed: Nov. 28, 2016

(86) PCT No.: PCT/JP2016/085189
§ 371 (c)(1),
(2) Date: Jul. 16, 2018

(87) PCT Pub. No.: WO2017/145475
PCT Pub. Date: Aug. 31, 2017

(65) Prior Publication Data
US 2019/0053857 A1    Feb. 21, 2019

(30) Foreign Application Priority Data

Feb. 24, 2016  (JP) .............................. JP2016-033031

(51) Int. Cl.
*A61B 34/20*   (2016.01)
*A61B 1/00*    (2006.01)
(Continued)

(52) U.S. Cl.
CPC ................ *A61B 34/20* (2016.02); *A61B 1/00* (2013.01); *A61B 1/0005* (2013.01);
(Continued)

(58) Field of Classification Search
CPC ..... A61B 1/00; A61B 1/0005; A61B 1/00188; A61B 1/042; A61B 1/045; A61B 1/3132; A61B 2034/2057; A61B 1/00149
See application file for complete search history.

(56) References Cited

U.S. PATENT DOCUMENTS 6,036,637 A * 3/2000 Kudo ................. A61B 1/00039
600/102
2007/0197865 A1* 8/2007 Miyake .................. A61B 90/36
600/109
(Continued)

FOREIGN PATENT DOCUMENTS

JP    8-164148 A    6/1996
JP    8-187246 A    7/1996
(Continued)

OTHER PUBLICATIONS

International Search Report dated Jan. 17, 2017 in PCT/JP2016/085189 filed Nov. 28, 2016.
(Continued)

*Primary Examiner* — Timothy J Neal
*Assistant Examiner* — Jae Woo
(74) *Attorney, Agent, or Firm* — Xsensus LLP

(57) ABSTRACT

[Problem] A surgical apparatus of the related art controls only the cropping position of a captured image, and thus only executes a limited range of image control in laparoscopic surgery.
[Solution] A medical information processing apparatus including: an image control section that controls processing of a captured image from a camera; and an arm control
(Continued)

section that controls a motion of an arm that supports the camera. One of the image control section and the arm control section executes control on a basis of control information from another control section.

16 Claims, 12 Drawing Sheets

(51) Int. Cl.
    *A61B 1/04*         (2006.01)
    *A61B 1/045*       (2006.01)
    *A61B 1/313*       (2006.01)
    *H04N 5/232*      (2006.01)

(52) U.S. Cl.
    CPC ............ *A61B 1/00188* (2013.01); *A61B 1/04* (2013.01); *A61B 1/042* (2013.01); *A61B 1/045* (2013.01); *A61B 1/3132* (2013.01); *H04N 5/23296* (2013.01); *A61B 2034/2057* (2016.02); *A61B 2034/2065* (2016.02)

(56) References Cited

U.S. PATENT DOCUMENTS

| | | | |
|---|---|---|---|
| 2009/0248036 A1* | 10/2009 | Hoffman | A61B 1/00149 606/130 |
| 2010/0228249 A1* | 9/2010 | Mohr | A61B 18/1206 606/41 |
| 2014/0024948 A1* | 1/2014 | Shida | G02B 23/2469 600/476 |
| 2014/0323803 A1 | 10/2014 | Hoffman et al. | |
| 2015/0080655 A1* | 3/2015 | Peterson | A61B 1/00105 600/112 |
| 2015/0297313 A1* | 10/2015 | Reiter | A61B 5/7267 600/408 |
| 2016/0203602 A1* | 7/2016 | Hayashi | A61B 1/00009 382/128 |
| 2017/0027416 A1* | 2/2017 | Hayashi | A61B 34/75 |
| 2019/0327394 A1* | 10/2019 | Ramirez Luna | H04N 13/106 |

FOREIGN PATENT DOCUMENTS

| | | |
|---|---|---|
| JP | 9-28713 A | 2/1997 |
| JP | 10-118076 A | 5/1998 |
| JP | 2001-197347 A | 7/2001 |
| JP | 2002-159444 A | 6/2002 |
| JP | 2002-172083 A | 6/2002 |
| JP | 2004-41778 A | 2/2004 |
| JP | 2005046233 A | 2/2005 |
| JP | 2007-222238 A | 9/2007 |
| JP | 2008-252348 A | 10/2008 |
| JP | 2015-139646 A | 8/2015 |
| KR | 10-2010-0112310 A | 10/2010 |
| KR | 10-2016-0008130 A | 1/2016 |

OTHER PUBLICATIONS

Extended European Search Report dated Jan. 7, 2019 in the corresponding European Application No. 16891631.0.

* cited by examiner

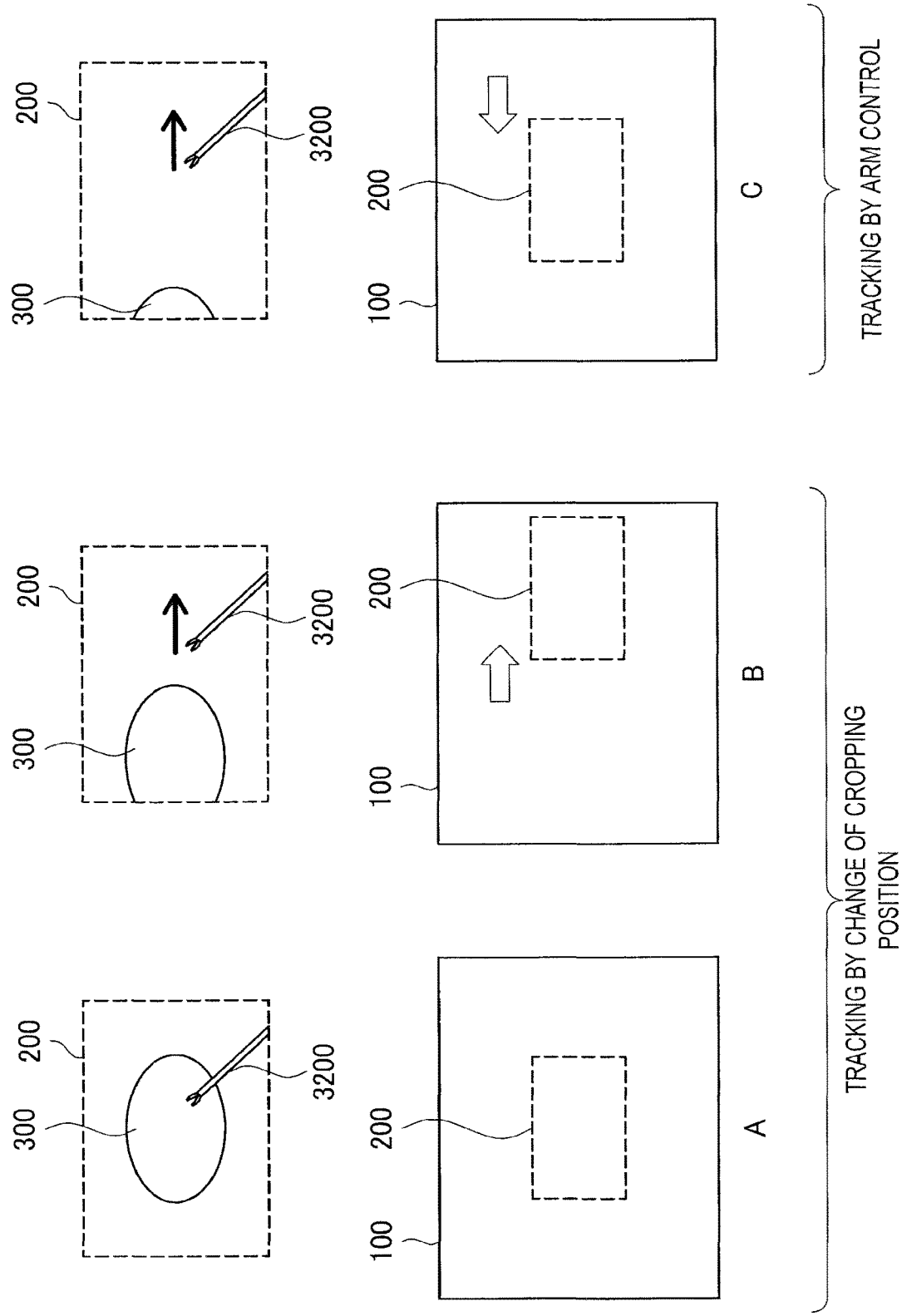

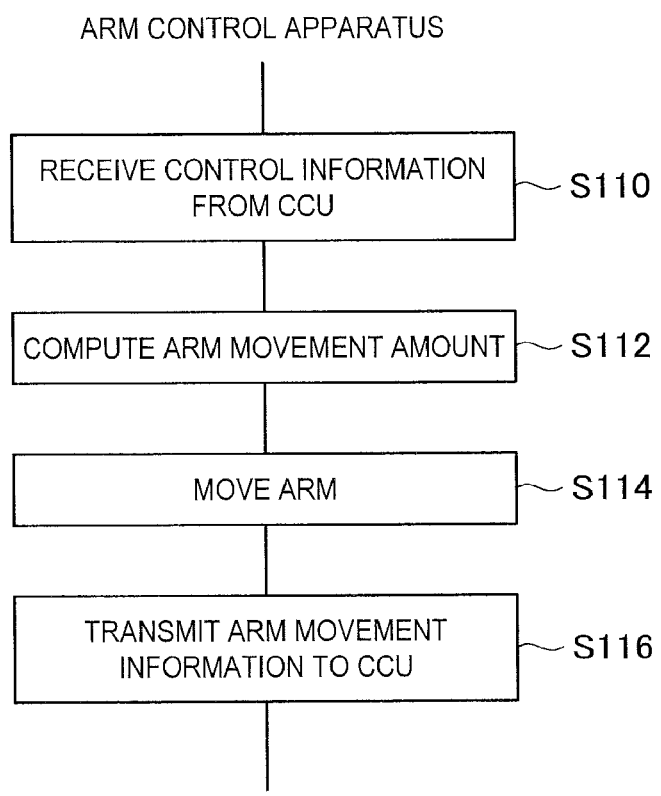

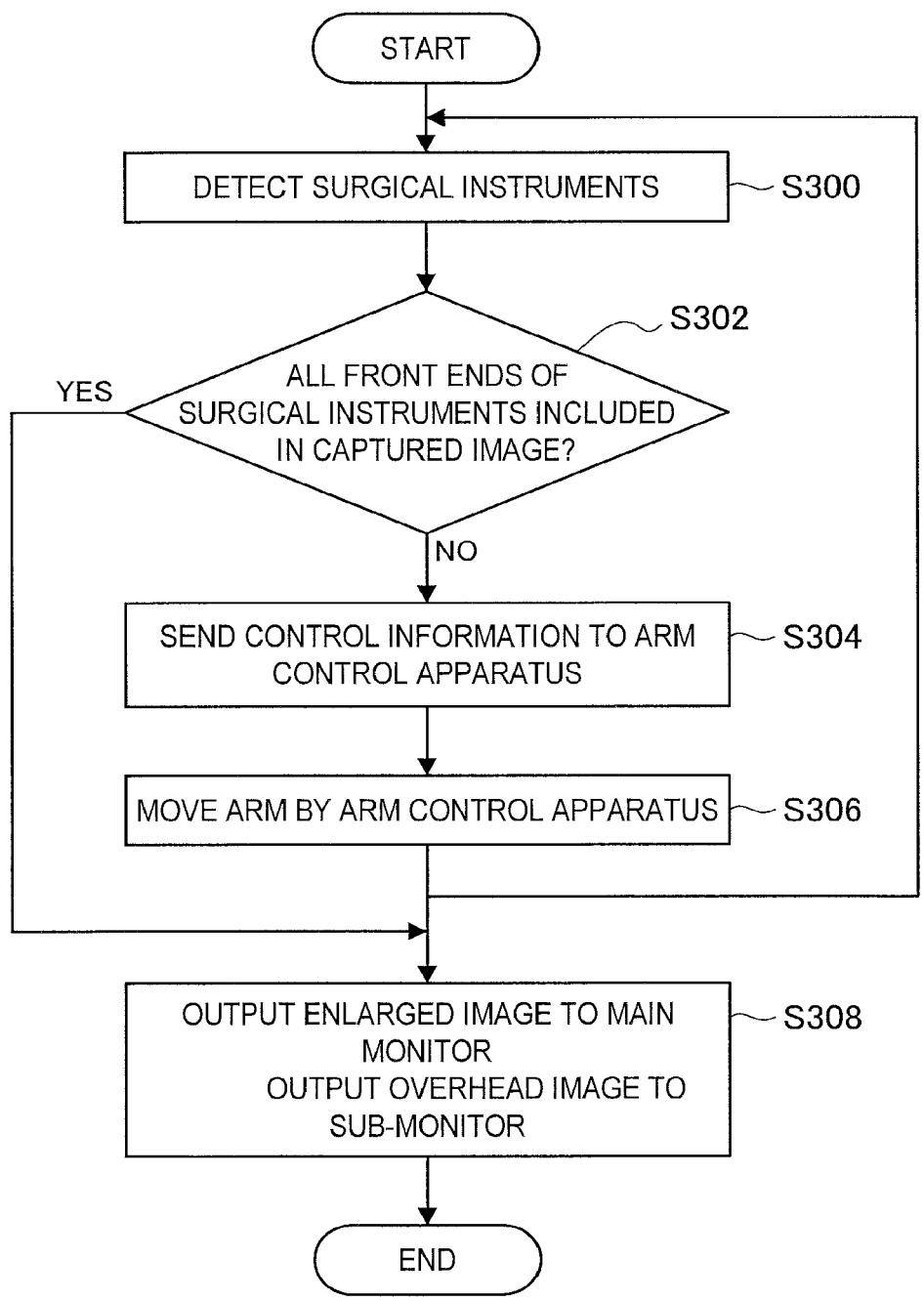

MEDICAL INFORMATION PROCESSING APPARATUS, INFORMATION PROCESSING METHOD, AND MEDICAL INFORMATION PROCESSING SYSTEM

TECHNICAL FIELD

The present disclosure relates to a medical information processing apparatus, an information processing method, and a medical information processing system.

BACKGROUND ART

Recently, many endoscopic surgeries using endoscopes with little burden on the patient are being performed. In an endoscopic surgery, the endoscope is used to capture an image inside the abdominal cavity of the patient, and surgery is performed while displaying the captured image captured by the endoscope on a display.

Patent Literature 1 discloses an endoscopic surgical apparatus used in endoscopic surgery as described above. The surgical apparatus disclosed in Patent Literature 1 detects the position of the front end of a treatment tool from a captured image of the endoscope, and on the basis of the detection result, a part of the captured image is cropped and enlarged for display on a monitor.

CITATION LIST

Patent Literature

Patent Literature 1: JP H8-164148A

DISCLOSURE OF INVENTION

Technical Problem

The surgical apparatus disclosed in Patent Literature 1 controls the cropping position of the captured image. However, with the cropping position of the captured image, the range which can be imaged is limited in endoscopic surgery.

Accordingly, the present disclosure proposes an information processing apparatus that executes a variety of imaging desired by an operator or a surgeon by controlling the motion of an arm section that supports a camera.

Solution to Problem

According to the present disclosure, there is provided a medical information processing apparatus including: an image control section that controls processing of a captured image from a camera; and an arm control section that controls a motion of an arm section that supports the camera. One of the image control section and the arm control section executes control on a basis of control information from another control section.

Advantageous Effects of Invention

According to the present disclosure as described above, a variety of imaging desired by the operator or the surgeon can be executed.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 3 is a block diagram illustrating part of the configuration of the surgery system illustrated in FIG. 1.

FIG. 4B is a flowchart illustrating an example of the process of the arm control apparatus in an operation of tracking a surgical instrument in the present disclosure.

FIG. 11 is a flowchart illustrating the display image sorting operation based on the type of surgical instrument illustrated in FIG. 10.

MODE(S) FOR CARRYING OUT THE INVENTION

Figure 1:
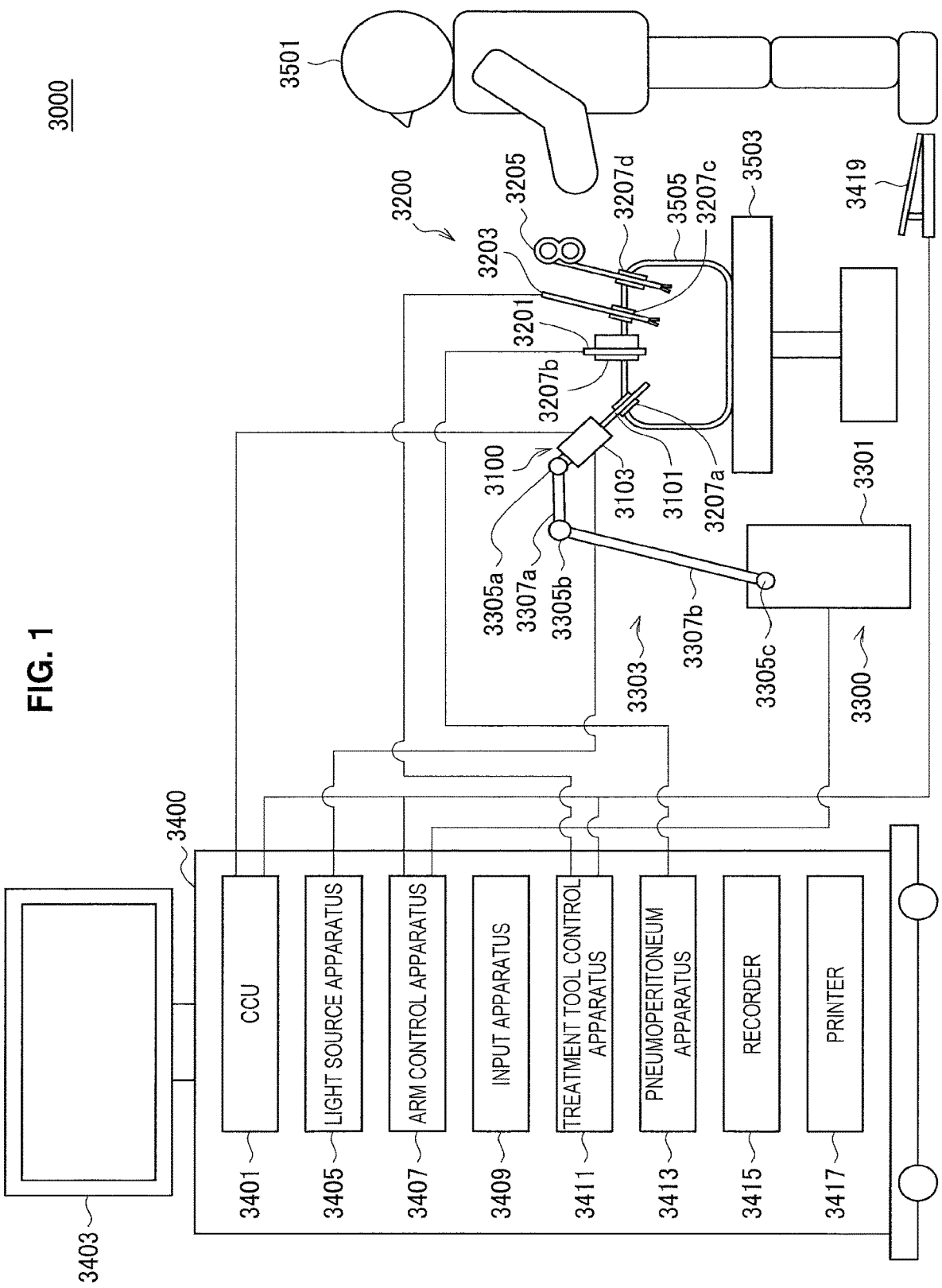
FIG. 1 is a diagram illustrating an example of a schematic configuration of an endoscopic surgery system.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Hereinafter, the description will proceed in the following order.

1. Exemplary configuration of surgery system
2. First embodiment
3. Second embodiment
4. Third embodiment
5. Supplement
6. Conclusion 1. Exemplary Configuration of Surgery System The technology according to the present disclosure may be applied to various products. For example, the technology according to the present disclosure may be applied to an endoscopic surgery system.

FIG. 1 is a diagram illustrating an example of a schematic configuration of an endoscopic surgery system 3000 to which the technology according to the present disclosure may be applied. FIG. 1 illustrates a situation in which a surgeon (doctor) 3501 is using an endoscopic surgery system 3000 to perform surgery on a patient 3505 lying on a patient bed 3503. As illustrated in the diagram, the endoscopic surgery system 3000 includes an endoscope 3100, other surgical instruments 3200, a support arm apparatus 3300 that supports the endoscope 3100, and a cart 3400 on which various apparatus for endoscopic surgery are provided.

In endoscopic surgery, instead of opening up the abdomen by cutting the abdominal wall, tubular hole-opening tools called trocars 3207a to 3207d are used to puncture the abdominal wall in multiple places. Subsequently, the lens tube 3101 of the endoscope 3100 and other surgical instruments 3200 are inserted into the body cavity of the patient 3505 from the trocars 3207a to 3207d. In the illustrated example, a pneumoperitoneum tube 3201, an energy treatment tool 3203, and forceps 3205 are inserted into the body cavity of the patient 3505 as the other surgical instruments 3200. Further, the energy treatment tool 3203 is a treatment tool that makes incisions into and ablates tissues, or seals blood vessels or the like, with a high-frequency electric current or ultrasonic vibration. However, the surgical instruments 3200 illustrated in the diagram are merely an example, and any of various types of surgical instruments typically used in endoscopic surgery, such as tweezers and retractors, for example, may also be used as the surgical instruments 3200.

An image of the operating site inside the body cavity of the patient 3505 taken by the endoscope 3100 is displayed on a display apparatus 3403. The surgeon 3501 uses the energy treatment tool 3203 and the forceps 3205 to perform treatments, such as excising an affected area, for example, while watching in real time the image of the operating site displayed on the display apparatus 3403. Note that, although omitted from the diagram, the pneumoperitoneum tube 3201, the energy treatment tool 3203, and the forceps 3205 are supported by a person such as the surgeon 3501 or an assistant during surgery.

(Support Arm Apparatus)

The support arm apparatus 3300 is provided with an arm section 3303 that extends from a base section 3301. In the illustrated example, the arm section 3303 includes joint sections 3305a, 3305b, and 3305c, as well as links 3307a and 3307b, and is driven by control from an arm control apparatus 3407. The endoscope 3100 is supported by the arm section 3303, with the position and attitude controlled thereby. With this arrangement, locking of the endoscope 3100 in a stable position may be realized.

(Endoscope)

The endoscope 3100 includes a lens tube 3101 having a region of certain length from the front end that is inserted into the body cavity of the patient 3505, and a camera head 3103 connected to the base end of the lens tube 3101. The example illustrates the endoscope 3100 configured as what is called a rigid scope having a rigid lens tube 3101. However, the endoscope 3100 may also be configured as what is called a flexible scope having a flexible lens tube 3101.

On the front end of the lens tube 3101, there is provided an opening into which an objective lens is fitted. A light source apparatus 3405 is connected to the endoscope 3100. Light generated by the light source apparatus 3405 is guided up to the front end of the lens tube by a light guide extending inside the lens tube 3101, and is radiated through the objective lens towards an observation target inside the body cavity of the patient 3505. Note that the endoscope 3100 may be a forward-viewing scope, and may also be an oblique-viewing scope or a side-viewing scope.

An optical system and an image sensor are provided inside the camera head 3103, and reflected light (observation light) from the observation target is condensed onto the image sensor by the optical system. Observation light is photoelectrically converted by the image sensor, and an electrical signal corresponding to the observation light, or in other words, an image signal corresponding to the observed image, is generated. The image signal is transmitted as RAW data to a camera control unit (CCU) 3401. Note that the camera head 3103 is provided with a function of adjusting the magnification and the focal length by appropriately driving the optical system.

Note that, to support stereoscopic vision (3D display) or the like, for example, multiple image sensors may be provided in the camera head 3103. In this case, multiple relay optical subsystems are provided inside the lens tube 3101 to guide the observation light to each of the multiple image sensors.

(Various Apparatus Provided on Cart)

The CCU 3401 includes a central processing unit (CPU), a graphics processing unit (GPU) and the like, and centrally controls the operation of the endoscope 3100 and the display apparatus 3403. Specifically, the CCU 3401 subjects an image signal received from the camera head 3103 to various types of image processing for displaying an image based on the image signal, such as a development process (demosaicing process), for example. The CCU 3401 provides an image signal that has been subjected to such image processing to the display apparatus 3403. Also, the CCU 3401 transmits a control signal to the camera head 3103 to control the driving thereof. The control signal may include information related to imaging conditions, such as the magnification and the focal length.

The display apparatus 3403, under control by the CCU 3401, displays an image based on an image signal subjected to image processing by the CCU 3401. In a case in which the endoscope 3100 supports imaging at a high resolution such as 4K (3840 horizontal pixels×2160 vertical pixels) or 8K (7680 horizontal pixels×4320 vertical pixels), and/or supports 3D display, for example, an apparatus compatible with each and capable of high-resolution display and/or capable of 3D display may be used as the display apparatus 3403. In the case in which imaging at a high resolution such as 4K or 8K is supported, a device with a size of 55 inches or more may be used as the display apparatus 3403 to thereby obtain an even deeper sense of immersion. Also, depending on the application, multiple display apparatus 3403 with different resolutions and sizes may also be provided.

The light source apparatus 3405 includes a light source such as a light-emitting diode (LED), for example, and supplies the endoscope 3100 with irradiating light when imaging the operating site.

The arm control apparatus 3407 includes a processor such as a CPU, for example, and by operating in accordance with a predetermined program, controls the driving of the arm section 3303 of the support arm apparatus 3300 in accordance with a predetermined control method.

The input apparatus 3409 is an input interface with respect to the endoscopic surgery system 3000. Through the input apparatus 3409, the user is able to input various information and instructions into the endoscopic surgery system 3000. For example, through the input apparatus 3409, the user inputs various information related to surgery, such as physical information about the patient, and information about surgical procedures. As another example, through the input apparatus 3409, the user inputs instructions to drive the arm section 3303, instructions to change the imaging conditions of imaging by the endoscope 3100 (such as the type of irradiating light, the magnification, and the focal length), instructions to drive the energy treatment tool 3203, and the like.

The type of the input apparatus 3409 is not limited, and the input apparatus 3409 may be any of various known types of input apparatus. For example, a mouse, a keyboard, a touch panel, a switch, the footswitch 3419, and/or a lever and the like may be applied as the input apparatus 3409. In the case in which a touch panel is used as the input apparatus 3409, the touch panel may be provided on the display screen of the display apparatus 3403.

Alternatively, the input apparatus 3409 is a device worn by the user, such as an eyeglasses-style wearable device or a head-mounted display (HMD), for example, and various types of input is performed in accordance with the user's gestures or gaze, or the like detected by these devices. Further, the input apparatus 3409 includes a camera capable of detecting motions of the user. Various types of input is performed in accordance with the user's gestures or gaze detected from a picture imaged by the camera. Furthermore, the input apparatus 3409 includes a microphone capable of picking up the user's speech. Various types of input is performed by speech through the microphone. In this way, by configuring the input apparatus 3409 to be capable of accepting the input of various types of information in a non-contact manner, a user belonging to a clean area in particular (for example, the surgeon 3501) becomes able to operate equipment belonging to an unclean area in a non-contact manner. Also, since the user becomes able to operate equipment without taking one's hands away from the tools the user is holding, user convenience is improved.

A treatment tool control apparatus 3411 controls the driving of the energy treatment tool 3203 to cauterize or make incisions into tissue, seal blood vessels, or the like. A pneumoperitoneum apparatus 3413 delivers gas into the body cavity through the pneumoperitoneum tube 3201 to inflate the body cavity of the patient 3505 for the purpose of securing a field of view for the endoscope 3100 and securing a workspace for the surgeon. A recorder 3415 is an apparatus capable of recording various types of information related to surgery. A printer 3417 is an apparatus capable of printing out various types of information related to surgery in various formats, such as text, images, or graphs.

Hereinafter, the characteristic configuration in particular in the endoscopic surgery system 3000 will be described in further detail.

(Support Arm Apparatus)

The support arm apparatus 3300 is provided with a base section 3301 which acts as a base, and the arm section 3303 which extends from the base section 3301. In the illustrated example, the arm section 3303 includes multiple joint sections 3305a, 3305b, and 3305c, as well as multiple links 3307a and 3307b joined by the joint section 3305b, but in FIG. 1, for the sake of simplicity, the configuration of the arm section 3303 is illustrated in a simplified manner. In actuality, the shapes, numbers, and arrangement of the joint sections 3305a to 3305c and the links 3307a and 3307b, the directions of the rotation axes of the joint sections 3305a to 3305c, and the like may be set appropriately so that the arm section 3303 has the desired degrees of freedom. For example, the arm section 3303 preferably may be configured to have six or more degrees of freedom. With this arrangement, it is possible to move the endoscope 3100 freely within the movable range of the arm section 3303, and thus it becomes possible to insert the lens tube 3101 of the endoscope 3100 into the body cavity of the patient 3505 from a desired direction.

The joint sections 3305a to 3305c are provided with actuators, and the joint sections 3305a to 3305c are configured to be rotatable about a certain rotation axis in accordance with the driving of the actuators. By controlling the driving of the actuators with the arm control apparatus 3407, the rotational angle of each of the joint sections 3305a to 3305c is controlled, and the driving of the arm section 3303 is controlled. With this arrangement, the position and the attitude of the endoscope 3100 may be controlled. At this point, the arm control apparatus 3407 is able to control the driving of the arm section 3303 with any of various known types of control methods, such as force control or position control.

For example, by having the surgeon 3501 perform appropriate operation input via an input apparatus 3409 (including a footswitch 3419), the driving of the arm section 3303 may be controlled appropriately by the arm control apparatus 3407 in accordance with the operation input, and the position and the attitude of the endoscope 3100 may be controlled. By such control, after moving the endoscope 3100 on the front end of the arm section 3303 from an arbitrary position to an arbitrary position, the endoscope 3100 can be supported securely at the position after the move. Note that the arm section 3303 may be operated by what is called a master-slave method. In this case, the arm section 3303 may be operated remotely by a user via the input apparatus 3409 installed in a location distanced from the operating room.

Further, in the case in which force control is applied, the arm control apparatus 3407 receives the external force by the user, and may execute what is called power assist control, in which the actuators of each of the joint sections 3305a to 3305c are driven so that the arm section 3303 moves smoothly following the external force. With this arrangement, when the user moves the arm section 3303 while touching the arm section 3303 directly, the arm section 3303 can be moved with comparatively light force. Consequently, it becomes possible to move the endoscope 3100 more intuitively with a simpler operation, and convenience for the user can be improved.

Herein, in endoscopic surgery, typically the endoscope 3100 has been supported by a doctor called a scopist. In contrast, by using the support arm apparatus 3300, it becomes possible to keep the position of the endoscope 3100 fixed more reliably without manual work, and thus image of the operating site can be obtained consistently, making it possible to perform surgery smoothly.

Note that the arm control apparatus 3407 does not necessarily have to be provided on the cart 3400. Also, the arm control apparatus 3407 does not necessarily have to be a single device. For example, the arm control apparatus 3407 may also be proved respectively in each of the joint sections 3305a to 3305c of the arm section 3303 of the support arm apparatus 3300, and the multiple arm control apparatus 3407 may cooperate with each other to realize driving control of the arm section 3303.

(Camera Head and CCU)

Figure 2:
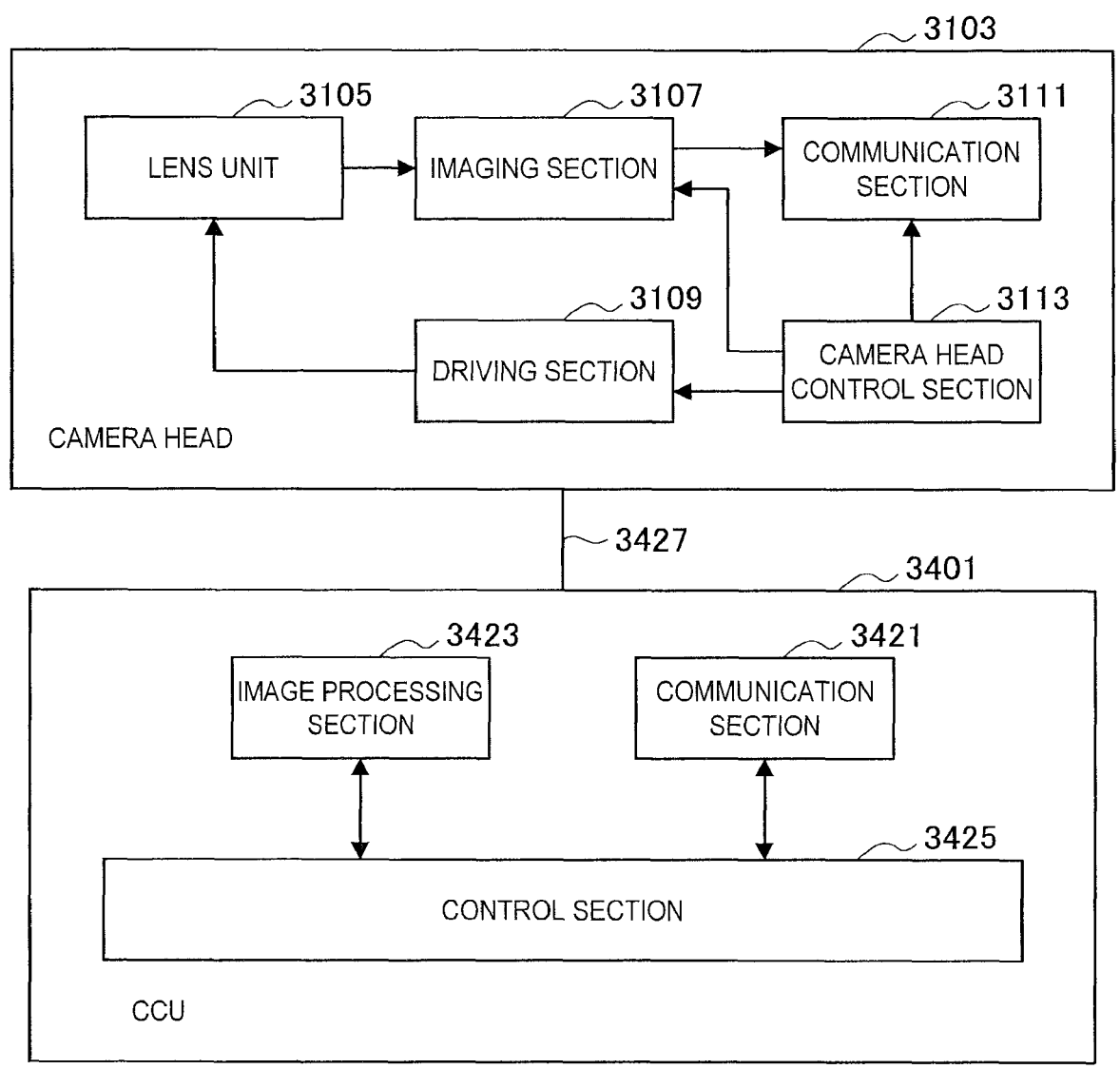
FIG. 2 is a block diagram illustrating an example of a functional configuration of the camera head and the CCU illustrated in FIG. 1.

The functions of the camera head 3103 and the CCU 3401 of the endoscope 3100 will be described in further detail with reference to FIG. 2. FIG. 2 is a block diagram illustrating an example of a functional configuration of the camera head 3103 and the CCU 3401 illustrated in FIG. 1.

Referring to FIG. 2, functionally, the camera head 3103 includes a lens unit 3105, an imaging section 3107, a driving section 3109, a communication section 3111, and a camera head control section 3113. Also, functionally, the CCU 3401 includes a communication section 3421, an image processing section 3423, and a control section 3425. The camera head 3103 and the CCU 3401 are bidirectionally communicably connected by a transmission cable 3427.

First, a functional configuration of the camera head 3103 will be described. The lens unit 3105 is an optical system provided in the part that connects to the lens tube 3101. Observation light taken in from the front end of the lens tube 3101 is guided up to the camera head 3103, and is incident on the lens unit 3105. The lens unit 3105 includes a combination of multiple lenses, including a zoom lens and a focus lens. The optical characteristics of the lens unit 3105 are adjusted to condense observation light onto the photosensitive face of an image sensor in the imaging section 3107. Also, the zoom lens and the focus lens are configured to be able to move position on the optical axis to adjust the magnification and the focus of the captured image.

The imaging section 3107 includes an image sensor, and is disposed downstream from the lens unit 3105. Observation light passing through the lens unit 3105 is condensed onto the photosensitive face of the image sensor, and by photoelectric conversion, an image signal corresponding to the observed image is generated. The image signal generated by the imaging section 3107 is provided to the communication section 3111.

For the image sensor included in the imaging section 3107, a complementary metal-oxide semiconductor (CMOS) type image sensor having a Bayer array to enable color imaging is used, for example. Note that a sensor capable of capturing high-resolution images of 4K or greater may be used as the image sensor, for example. By obtaining a high-resolution image of the operating site, the surgeon 3501 becomes able to grasp the state of the operating site in greater detail, and proceed with surgery more smoothly.

Also, the image sensor included in the imaging section 3107 is configured to include a pair of image sensors for acquiring an image signal for each of the right eye and the left eye corresponding to 3D display. By presenting a 3D display, the surgeon 3501 becomes able to grasp the depth of biological tissue at the operating site more accurately. Note that if the imaging section 3107 has a multi-chip configuration, the lens unit 3105 likewise is provided with multiple subsystems corresponding to each of the image sensors.

Also, the imaging section 3107 does not necessarily have to be provided in the camera head 3103. For example, the imaging section 3107 may also be provided inside the lens tube 3101, directly behind the objective lens.

The driving section 3109 includes actuators, and under control from the camera head control section 3113, moves the zoom lens and the focus lens of the lens unit 3105 by a predetermined distance along the optical axis. With this arrangement, the magnification and the focus of the image captured by the imaging section 3107 may be adjusted appropriately.

The communication section 3111 includes a communication apparatus for transmitting and receiving various information to and from the CCU 3401. The communication section 3111 transmits an image signal obtained from the imaging section 3107 as RAW data to the CCU 3401 through the transmission cable 3427. At this point, to display the captured image of the operating site with low latency, the image signal preferably is transmitted by optical communication. This is because during surgery, the surgeon 3501 performs surgery while observing the state of the affected area via the captured image, and thus for safer and more reliable surgery, there is demand for the moving image of the operating site to be displayed as close to real-time as possible. In the case in which optical communication is conducted, the communication section 3111 is provided with a photoelectric conversion module that converts an electrical signal into an optical signal. The image signal is converted into an optical signal by the photoelectric conversion module, and then transmitted to the CCU 3401 through the transmission cable 3427.

Also, the communication section 3111 receives, from the CCU 3401, a control signal for controlling the driving of the camera head 3103. The control signal includes information related to imaging parameters, such as information specifying the frame rate of the captured image, information specifying the exposure value during imaging, and/or information specifying the magnification and focus of the captured image, for example. The communication section 3111 provides the received control signal to the camera head control section 3113. Note that the control signal from the CCU 3401 may also be transmitted by optical communication. In this case, the communication section 3111 is provided with a photoelectric conversion module that converts an optical signal into an electrical signal, whereby the control signal is converted into an electrical signal by the photoelectric conversion module, and then provided to the camera head control section 3113.

Note that the above imaging parameters such as the frame rate, the exposure value, the magnification, and the focus are set automatically by the control section 3425 of the CCU 3401 on the basis of the acquired image signal. In other words, what are called an auto exposure (AE) function, an auto focus (AF) function, and an auto white balance (AWB) function are provided in the endoscope 3100.

The camera head control section 3113 controls the driving of the camera head 3103 on the basis of a control signal from the CCU 3401 received via the communication section 3111. For example, the camera head control section 3113 controls the driving of the image sensor of the imaging section 3107, on the basis of information specifying the frame rate of the captured image and/or information specifying the exposure during imaging. As another example, the camera head control section 3113 appropriately moves the zoom lens and the focus lens of the lens unit 3105 via the driving section 3109, on the basis of information specifying the magnification and the focus of the captured image. Additionally, the camera head control section 3113 may also be provided with a function of storing information for identifying the lens tube 3101 and the camera head 3103.

Note that by disposing parts of the configuration, such as the lens unit 3105 and the imaging section 3107, inside a highly airtight and waterproof sealed structure, the camera head 3103 can be made to withstand an autoclaving sterilization process.

Next, a functional configuration of the CCU 3401 will be described. The communication section 3421 includes a communication apparatus for transmitting and receiving various information to and from the camera head 3103. The communication section 3421 receives an image signal transmitted from the camera head 3103 through the transmission cable 3427. At this point, as described earlier, the image signal preferably may be transmitted by optical communication. In this case, to support optical communication, the communication section 3421 is provided with a photoelectric conversion module that converts an optical signal into an electrical signal. The communication section 3421 provides the image signal converted into an electrical signal to the image processing section 3423.

Also, the communication section 3421 transmits, to the camera head 3103, a control signal for controlling the driving of the camera head 3103. The control signal may also be transmitted by optical communication.

The image processing section 3423 performs various types of image processing on the image signal, which is RAW data transmitted from the camera head 3103. The image processing includes any of various known types of signal processing, such as a development process, an image quality-improving process (such as a band enhancement process, a super-resolution process, a noise reduction (NR) process, and/or a shake correction process), and/or an enlargement process (digital zoom process), for example. Also, the image processing section 3423 executes a wave detection process on the image signal to execute AE, AF, and AWB.

The image processing section 3423 includes a processor such as a CPU or a GPU, and by having the processor operate in accordance with a predetermined program, the image processing and wave detection process described above may be executed. Note that in the case in which the image processing section 3423 includes multiple GPUs, the image processing section 3423 appropriately divides up information related to the image signal, and executes image processing in parallel with the multiple GPUs.

The control section 3425 executes various types of control related to the imaging of the operating site by the endoscope 3100 and the display of the captured image therefrom. For example, the control section 3425 generates a control signal for controlling the driving of the camera head 3103. At this point, in a case in which imaging parameters are input by the user, the control section 3425 generates a control signal on the basis of the input by the user. Alternatively, in a case in which the endoscope 3100 is provided with an AE function, an AF function, and an AWB function, the control section 3425 appropriately computes an optimal exposure value, focal length, and white balance in accordance with the results of the wave detection process by the image processing section 3423, and generates a control signal.

In addition, the control section 3425 causes the display apparatus 3403 to display an image of the operating site on the basis of the image signal subjected to image processing by the image processing section 3423. At this point, the control section 3425 uses any of various types of image technology to recognize various objects in the operating site image. For example, by detecting the edge shapes, colors, and the like of objects included in the operating site image, the control section 3425 is able to recognize surgical instruments such as forceps, specific biological sites, hemorrhaging, mist during usage of the energy treatment tool 3203, and the like. When causing the display apparatus 3403 to display an image of the operating site, the control section 3425 uses the recognition results to overlay various surgical assistance information onto the image of the operating site. By overlaying surgical assistance information for display to be presented to the surgeon 3501, it becomes possible to proceed with surgery more safely and reliably.

The transmission cable 3427 that connects the camera head 3103 and the CCU 3401 is an electrical signal cable supporting the communication of electrical signals, optical fiber supporting optical communication, or a composite cable of the above.

Herein, in the illustrated example, communication is executed in a wired manner using the transmission cable 3427, but communication between the camera head 3103 and the CCU 3401 may also be executed wirelessly. In the case in which the communication between the two is executed wirelessly, it is no longer necessary to lay down the transmission cable 3427 inside the operating room, and thus a situation in which the movement of medical staff inside the operating room is impeded by the transmission cable 3427 may be resolved.

Note that herein, although the endoscopic surgery system 3000 is described as an example, the system to which technology according to the present disclosure may be applied is not limited to such an example. For example, the technology according to the present disclosure may also be applied to a flexible endoscopic system used for examinations, or a microscopic surgery system.

2. First Embodiment (Operation of Tracking Surgical Instruments)

The above illustrates a configuration of the endoscopic surgery system 3000 according to the present embodiment. In the following, an operation of tracking the surgical instruments 3200 in the endoscopic surgery system 3000 described above will be described. As described above, the CCU 3401 receives an image signal from the camera head 3103, and recognizes objects on the basis of the received image signal. In the endoscopic surgery system 3000 of the present disclosure, an operation of tracking the recognized surgical instruments 3200 is performed. Note that the camera head 3103 is one example of a camera that captures images, and the CCU 3401 is one example of an image control section that controls the processing of captured images.

Also, the detection of the surgical instruments 3200 is executed by detecting the edge shapes and/or colors and the like of the surgical instruments 3200 as described above. However, the detection of the surgical instruments 3200 may also be executed by another method, for example, the detection of the surgical instruments 3200 may also be executed by detecting a brightness gradient of the surgical instruments 3200. This is based on how the brightness gradient of the surgical instruments 3200 is uniform (fixed in a fixed direction), whereas the brightness gradient of objects other than the surgical instruments 3200, such as organs, is not uniform. Also, the detection of the surgical instruments 3200 may also be executed using machine learning. By using machine learning, the detection accuracy of the surgical instruments 3200 is improved with every use. This is extremely effective in a surgery system, that is, a system in which misrecognition is not acceptable.

FIG. 3 is a diagram illustrating an example of the operation of tracking a surgical instrument 3200 in the present disclosure. The frames indicated by the solid lines in FIG. 3 illustrate an image capture region 100 captured by the image sensor of the imaging section 3107. Also, the frames indicated by the dashed lines in FIG. 3 illustrate a display region 200 that the CCU 3401 transmits to the display apparatus 3403. Generally, the image capture region 100 is larger than the display region 200, the CCU 3401 crops the display region 200 from the image capture region 100, and the display region 200 is transmitted to the display apparatus 3403.

Also, the upper row of FIG. 3 illustrates how the display region 200 is displayed on the display apparatus 3403. The lower row of FIG. 3 illustrates the relationship between the image capture region 100 and the display region 200. The upper row of FIG. 3 illustrates how an imaging target 300, such as an organ of the patient 3505, and a surgical instrument 3200, such as the forceps 3205, are imaged.

A of FIG. 3 is the initial state, in which the vicinity of the front end of the surgical instrument 3200 is positioned in the center of the display region 200. Next, B of FIG. 3 illustrates how the surgical instrument 3200 moves to the right because of the surgeon 3501 or an assistant moving the surgical instrument 3200 or the like.

At this time, as illustrated in the lower row of FIG. 3B, the CCU 3401 shifts the cropping position of the display region 200 to the right, to track the motion of the detected surgical instrument 3200. In this way, by having the CCU 3401 change the cropping position of the display region 200 according to the motion of the surgical instrument 3200, the vicinity of the front end of the surgical instrument 3200 is kept in the center of the display region 200. Keeping the front end of the surgical instrument 3200 in the center of the display region 200 makes it easier for the surgeon 3501 and the assistant to perform treatment.

Next, C of FIG. 3 is a diagram illustrating the case in which the surgical instrument 3200 moves farther to the right from B of FIG. 3. In C of FIG. 3, the front end of the surgical instrument 3200 is positioned outside the range of the image capture region 100 in the initial state (the image capture region 100 of A and B). At this time, the CCU 3401 sends control information to the arm control apparatus 3407 to move the arm section 3303 and track the surgical instrument 3200. The arm control apparatus 3407 receiving the control information from the CCU 3401 moves the arm section 3303, and tracks the surgical instrument 3200. Note that the arm control apparatus 3407 is an example of an arm control section that controls the arm section 3303.

At this time, to keep the front end of the surgical instrument 3200 in the center of the display region 200, as illustrated in the lower row of FIG. 3C, the CCU 3401 shifts the cropping position of the display region 200 in the opposite direction (to the left in the lower diagram of FIG. 3C) of the movement direction (to the right in the upper diagram of FIG. 3C) of the forceps 3205. With this arrangement, the display region 200 becomes the center of the image capture region 100, and a region for executing the next change of the cropping position is secured.

In the changing of the cropping position of the display region 200 in this way, in the case of being unable to accommodate the motion of the surgical instrument 3200, the CCU 3401 transmits, to the arm control apparatus 3407, control information to move the arm section 3303. With this arrangement, tracking of the surgical instrument 3200 over a wider range becomes possible.

Note that, due to the rigidity of the arm section 3303, there is a possibility that camera shake may occur after arm movement. At this time, the CCU 3401 may be configured to correct this camera shake by changing the cropping position of the display region. The camera shake correction is executed by having the CCU 3401 execute image processing, or by attaching a gyro sensor to the arm section 3303.

Figure 4A:
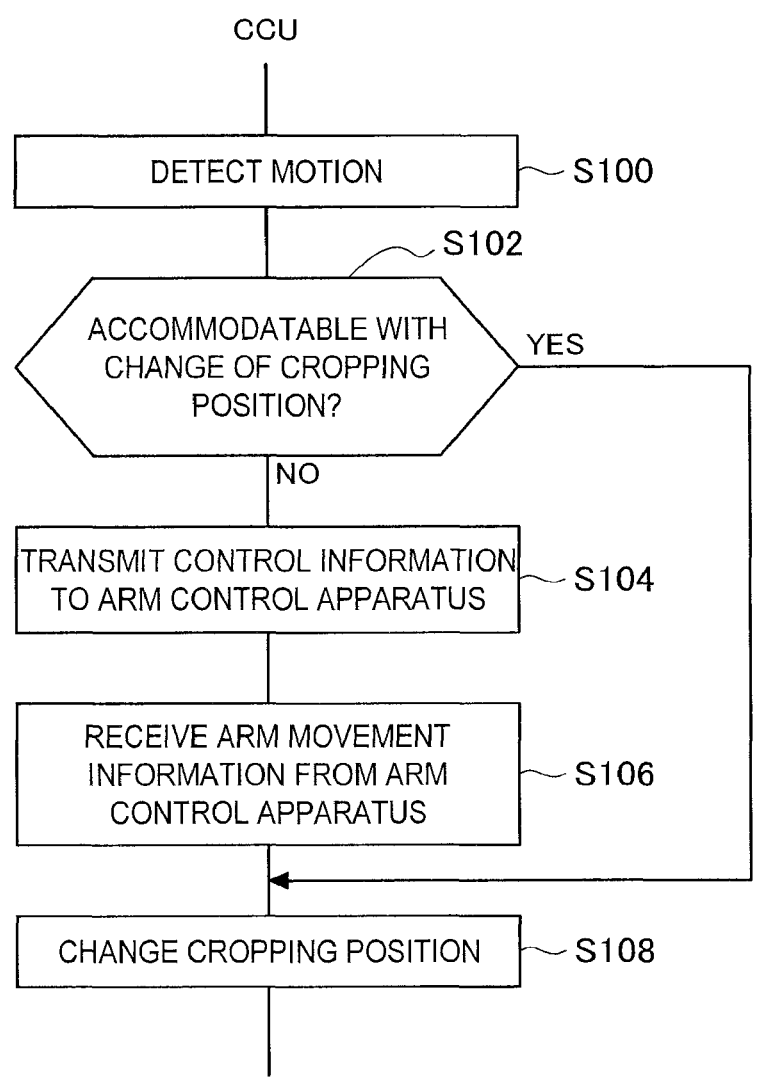
FIG. 4A is a flowchart illustrating an example of the process of the CCU in an operation of tracking a surgical instrument in the present disclosure.

FIG. 4A is a flowchart illustrating a process of the CCU 3401 in the operation of tracking the surgical instrument 3200 described above. In S100, the CCU 3401 detects the motion of the surgical instrument 3200. Next, in S102, the CCU 3401 determines whether or not the motion of the surgical instrument 3200 can be accommodated with a change of the cropping position of the display region 200.

In S102, in the case in which the motion of the surgical instrument 3200 can be accommodated with a change of the cropping position of the display region 200, the process proceeds to S108. In S108, the CCU 3401 changes the cropping position of the display region 200 according to the motion of the surgical instrument 3200.

In S102, in the case in which the motion of the surgical instrument 3200 cannot be accommodated with a change of the cropping position of the display region 200, the CCU 3401 sends control information for controlling the arm section 3303 to the arm control apparatus 3407 (S104).

When the arm control apparatus 3407 causes the arm section 3303 to move on the basis of the control information transmitted in S104, the arm control apparatus 3407 transmits arm movement information to the CCU 3401, and the CCU 3401 receives the arm movement information (S106).

Subsequently, in S108, the CCU 3401 changes the cropping position of the display region 200 on the basis of the arm movement information received from the arm control apparatus 3407. This change in the cropping position of the display region 200 is executed in the opposite direction of the direction of the movement of the arm section 3303 by S110.

Next, a process of the arm control apparatus 3407 in the operation of tracking the surgical instrument 3200 will be described. FIG. 4B is a flowchart illustrating a process of the arm control apparatus 3407 in the operation of tracking the surgical instrument 3200. When the CCU 3401 transmits control information in S104 of FIG. 4A, in S110, the arm control apparatus 3407 receives the control information.

Next, in S112, the arm control apparatus 3407 computes an arm movement amount by which to move the arm section 3303, on the basis of the control information received from the CCU 3401. Next, in S114, the arm control apparatus 3407 causes the arm section 3303 to move on the basis of the computed arm movement amount. In S114, when the arm section 3303 moves, in S116, the arm control apparatus 3407 sends arm movement information to the CCU 3401.

Note that the determination in S102 of FIG. 4A may be executed by various methods. For example, in the case in which a predetermined frame is preset inside the image capture region 100, and the front end of the surgical instrument 3200 moves out past the predetermined frame, the CCU 3401 may determine that the motion cannot be accommodated with a change of the cropping position of the display region 200. Also, the CCU 3401 may compute a motion vector of the surgical instrument 3200, and when the vector quantity of the motion vector is greater than a predetermined size, the CCU 3401 may determine that the motion cannot be accommodated with a change of the cropping position of the display region 200. In this case, the CCU 3401 may also transmit, to the arm control apparatus 3407, control information to move the arm at a speed and in a direction according to the computed vector quantity.

Also, in the example described above, in S116 of FIG. 4B, the arm control apparatus 3407 transmits arm movement information to the CCU 3401, and the CCU 3401 changes the cropping position on the basis of the arm movement information. However, the CCU 3401 may also detect the surgical instrument 3200 by image detection, and change the cropping position of the display region 200 so that the vicinity of the front end of the detected surgical instrument 3200 is in the center of the display region 200. Note that in the case in which the CCU 3401 changes the cropping position of the display region 200 on the basis of the arm movement information received in S106 of FIG. 4A, the CCU 3401 does not execute image detection, and thus the CCU 3401 is able to change the cropping position with a small processing load.

Figure 5:
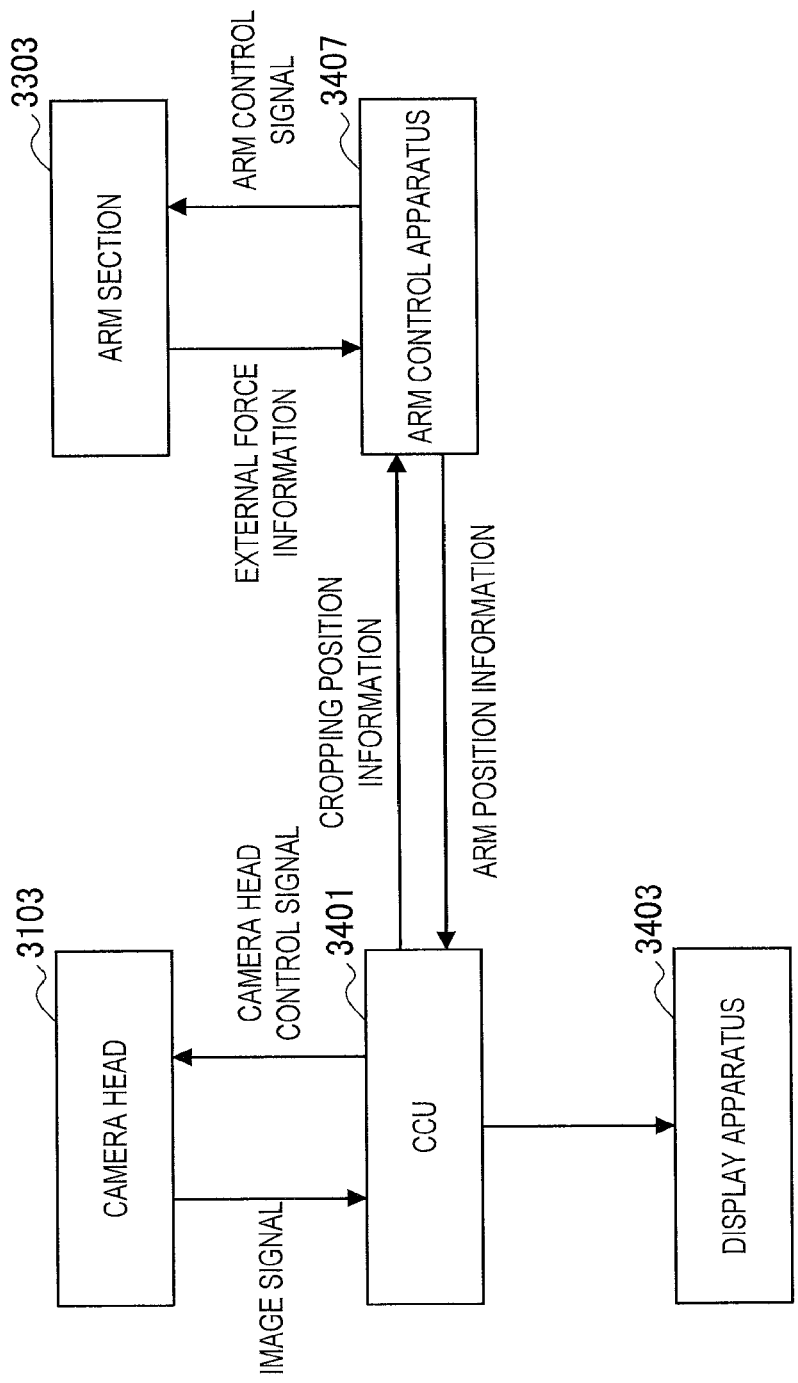
FIG. 5 is a flowchart illustrating an example of the operation of tracking a surgical instrument in the present disclosure.

The above describes an exemplary operation when tracking the surgical instrument 3200 in the surgery system of the present disclosure. In the following, information transmitted and received between each apparatus when tracking the surgical instrument 3200 described above will be illustrated with reference to FIG. 5.

As described above, the CCU 3401 receives an image signal from the camera head 3103, and processes the received image signal. In addition, the CCU 3401 transmits, to the camera head 3103, a camera head control signal for changing the magnification, focal length, or the like in the camera head 3103.

On the other hand, the arm control apparatus 3407 receives, from the arm section 3303, external force information indicating that an external force has been imparted to the arm section 3303. In addition, the arm control apparatus 3407 transmits, to the arm section 3303, an arm control signal for controlling the arm section 3303.

Between the CCU 3401 and the arm control apparatus 3407, control information for tracking the surgical instrument 3200 with the movement of the arm section 3303 described above is transmitted and received. As the control information illustrated in F104 of FIG. 4A, the CCU 3401 transmits position information about the surgical instrument 3200 or cropping position information about the display region 200 to the arm control apparatus 3407, for example. Also, as the control information, the CCU 3401 may transmit a vector quantity related to the motion of the detected surgical instrument 3200 to the arm control apparatus 3407. By having the CCU 3401 transmit the vector quantity, the arm control apparatus 3407 is able to control the operation of the arm section 3303 to match the speed and direction of the motion of the surgical instrument 3200.

Also, as the arm movement information illustrated in S116 of FIG. 4B, the arm control apparatus 3407 transmits position information, the movement speed, or the movement direction of the arm to the CCU 3401, for example. Additionally, as the arm movement information, the arm control apparatus 3407 may transmit a vector quantity related to the movement of the arm section 3303 to the CCU 3401. By having the 3407 transmit a vector quantity, the CCU 3401 is able to control the cropping position of the display region 200 to match the speed and direction of the motion of the arm section 3303.

Subsequently, the CCU 3401 processes the image signal received from the camera head 3103, crops the display region 200 from the image capture region 100, and transmits the cropped display region 200 to the display apparatus 3403.

Note that in S102 of FIG. 4, in the case in which the motion cannot be accommodated with a change of the cropping position, there is a possibility that the surgical instrument 3200 no longer exists inside the image capture region 100. In this case, the CCU 3401 may also store past frames of the image capture region 100 captured by the image sensor of the imaging section 3107. Subsequently, the CCU 3401 and the arm control apparatus 3407 use information related to the motion of the surgical instrument 3200 (for example, a motion vector quantity) in a past frame to execute the operation of tracking the surgical instrument 3200 by arm control. Also, in the case in which the surgical instrument 3200 has come to exist inside the image capture region 100, the arm control apparatus 3407 may also cooperate with the CCU 3401 to control the arm so that the front end of the surgical instrument 3200 is near the center of the image capture region 100.

(Summary of First Embodiment)

In the surgery system of the present disclosure as described above, the CCU 3401 not only tracks the surgical instrument 3200 by changing the cropping position of the display region 200, but in addition, the arm control apparatus 3407 causes the arm section 3303 that supports the camera head 3103 to move and track the surgical instrument 3200. By this arrangement, it becomes possible to track the surgical instrument 3200 even in cases of movement by the surgical instrument 3200 that cannot be accommodated with just a change of the cropping position of the display region 200 by the CCU 3401. Thus, the surgeon 3501 or assistant does not have to perform an operation to change the display region 200, allowing stress-free surgery to be performed.

3. Second Embodiment (Zoom Operation by Arm Control)

The above describes an example of an operation of tracking the surgical instrument 3200 by controlling the arm section 3303. In the following, a zoom operation by controlling the arm section 3303 will be described. As described above, by causing the zoom lens of the lens unit 3105 to move a predetermined distance along the optical axis, the endoscopic surgery system 3000 of the present disclosure is able to execute an optical zoom. Note that the term "zoom" described in the following includes the meaning of both "zoom in" and "zoom out", unless specifically noted otherwise.

The magnification at which the lens unit 3105 in the surgery system can enlarge images is limited in consideration of the lens becoming distorted by the sterilization process. Thus, the endoscopic surgery system 3000 of the present disclosure executes zoom by controlling the arm section 3303, in addition to an optical zoom or an electronic zoom by the camera head 3103. With this arrangement, zooming at an even larger or smaller magnification than the optical zoom becomes possible, and in addition, the zooming of an image at higher resolution than the digital zoom becomes possible. Note that the electronic zoom is executed by cutting out and enlarging a portion of an image captured by the imaging section 3107.

The characteristics of each of the optical zoom, the electronic zoom, and the zoom operation by arm control are illustrated in Table 1 below.

TABLE 1

|  | Response speed | Image quality | Obstacle handling |
| --- | --- | --- | --- |
| Optical zoom | Intermediate | Good | Possible |
| Electronic zoom | Fast | Poor | Possible |
| Arm control | Slow | Good | Not possible |

As illustrated in Table 1, for the response speed with respect to a zoom instruction from a user, electronic zoom is the fastest among the three zoom methods, whereas arm control is the slowest among the three zoom methods. Also, the response speed of optical zoom is intermediate between the two. Next, regarding image quality, zooming by optical zoom and arm control maintains high image quality, but with electronic zoom, the image quality is degraded. Also, regarding whether or not a zoom operation can be executed in the case in which an obstacle exists between the camera head 3103 and the subject (obstacle handling), optical zoom and electronic zoom are capable of the zoom operation, whereas the zoom operation by arm control is unavailable.

Figure 6A:
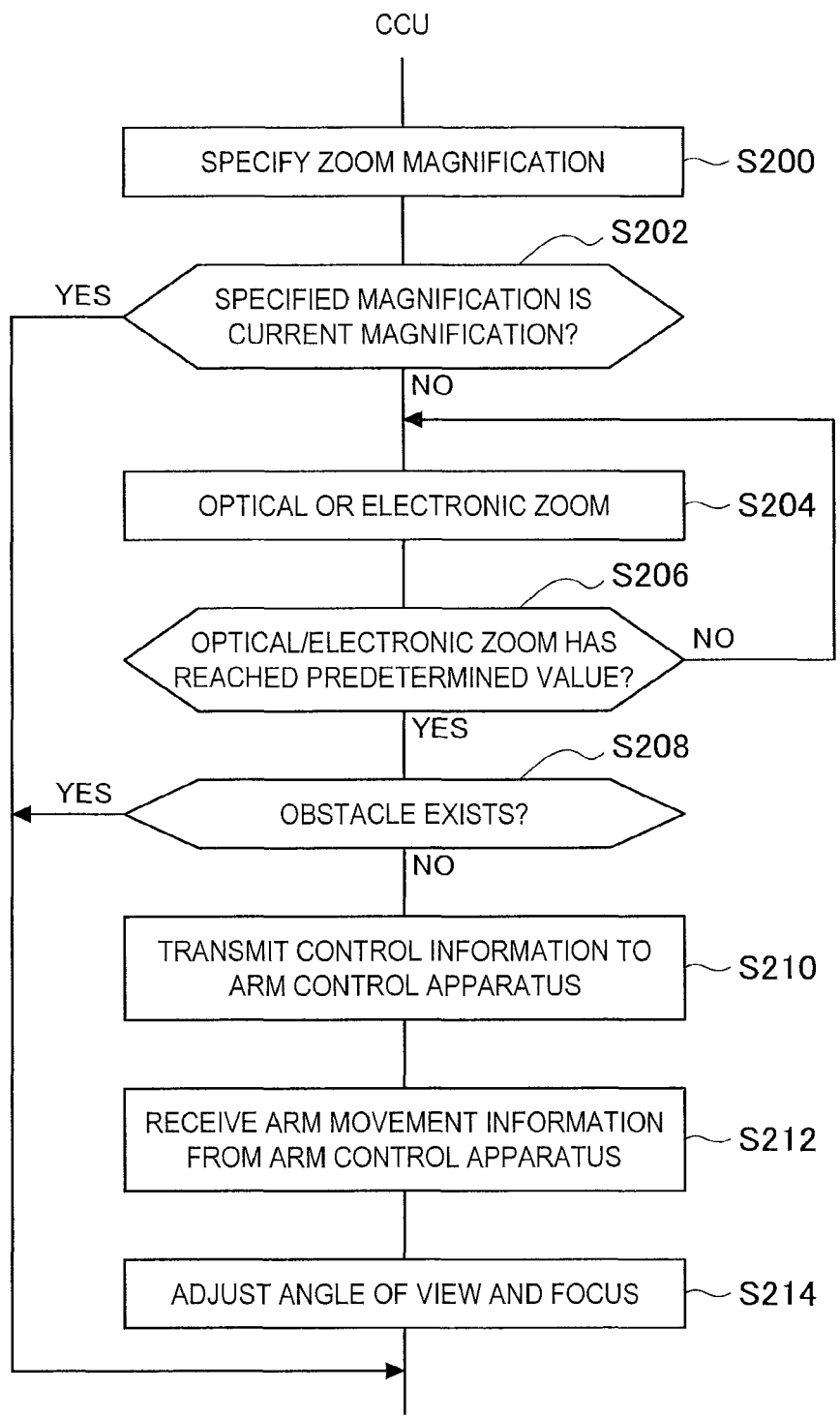
FIG. 6A is a flowchart illustrating an example of the process of the CCU in a zoom operation by arm control in the present disclosure.

The above illustrates the characteristics of each zoom operation. In the following, a zoom operation combining the zoom operation by the camera head 3103 and the zoom operation by arm control will be described. FIG. 6A is a flowchart illustrating an example of a process of the CCU 3401 in the zoom operation combining the zoom operation by the camera head 3103 and the zoom operation by arm control. Initially, in S200, the user inputs an instruction specifying a zoom magnification.

In S202, the CCU 3401 determines whether or not the magnification specified in S200 is the current magnification. In S202, if the CCU 3401 determines that the specified magnification is the current magnification, the process ends. On the other hand, in S202, if the CCU 3401 determines that the specified magnification is different from the current magnification, the process proceeds to S204.

In S204, the CCU 3401 executes the optical zoom or the electronic zoom on the basis of the magnification specified in S200. Next, the process proceeds to S206, and the CCU 3401 determines whether or not the magnification of the optical or electronic zoom has reached a predetermined value. In S206, in the case in which the CCU 3401 determines that the magnification of the optical or electronic zoom has not reached the predetermined value, the process returns to S204, and the zoom operation is repeated. In S206, in the case in which the CCU 3401 determines that the magnification of the optical or electronic zoom has reached the predetermined value, the process proceeds to S208.

In S208, the CCU 3401 determines whether or not there is an obstacle by executing image detection. In S208, if the CCU 3401 determines that there is an obstacle, since it is dangerous for the arm section 3303 to move, the process ends. On the other hand, in S208, if the CCU 3401 determines that there is no obstacle, the CCU 3401 sends the control information described above using FIGS. 4 and 5 to the arm control apparatus 3407 (S210).

When the arm control apparatus 3407 causes the arm section 3303 to move on the basis of the control information transmitted in S210, the arm control apparatus 3407 transmits arm movement information to the CCU 3401, and the CCU 3401 receives the arm movement information (S212). Additionally, in S214, the CCU 3401 adjusts the angle of view and the focus on the basis of the arm movement information received from the arm control apparatus 3407.

Figure 6B:
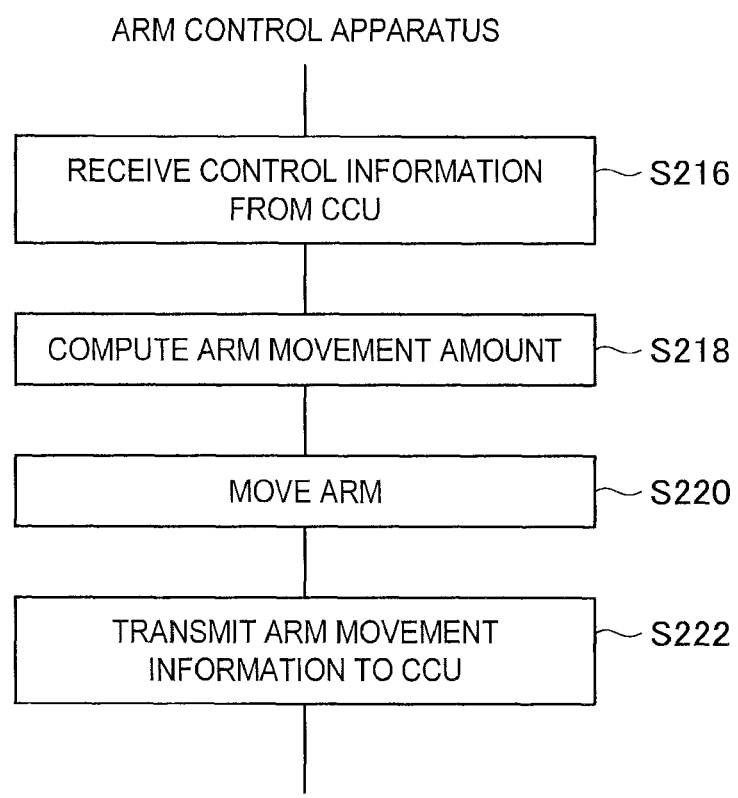
FIG. 6B is a flowchart illustrating an example of the process of the arm control apparatus in a zoom operation by arm control in the present disclosure.

Next, a process of the arm control apparatus 3407 in the zoom operation combining the zoom operation by the camera head 3103 and the zoom operation by arm control will be described. FIG. 6B is a flowchart illustrating a process of the arm control apparatus 3407 in the zoom operation combining the zoom operation by the camera head 3103 and the zoom operation by arm control. When the CCU 3401 transmits control information in S210 of FIG. 6A, in S216, the arm control apparatus 3407 receives the control information.

In S218, the arm control apparatus 3407 computes an arm movement amount by which to move the arm section 3303, on the basis of the control information received from the CCU 3401. Next, in S220, the arm control apparatus 3407 causes the arm section 3303 to move on the basis of the computed arm movement amount. In S220, when the arm section 3303 moves, in S222, the arm control apparatus 3407 sends the arm movement information described above using FIGS. 4 and 5 to the CCU 3401.

Note that the predetermined value in S206 may be a limit value of the magnification of the optical or electronic zoom. Also, the predetermined value in S206 may be a predetermined value below the limit value of the magnification of the optical or electronic zoom. In the case in which the predetermined value in S206 is a predetermined value below the limit value of the magnification of the optical or electronic zoom, the CCU 3401 is able to leave room to execute the optical or electronic zoom. With this arrangement, the CCU 3401 is able to switch the display image to an overhead image immediately by a user instruction.

Also, in the example described above, in S222 of FIG. 6B, the arm control apparatus 3407 transmits arm movement information to the CCU 3401, and the CCU 3401 adjusts the angle of view and the focus on the basis of the arm movement information. However, the CCU 3401 may also adjust the angle of view and the focus by a process based on the contrast or the like of the captured image.

The above describes an operational flow of the zoom operation by arm control in the endoscopic surgery system 3000 of the present disclosure. In the following the relationship between each zoom in the zoom operation of the present disclosure illustrated in FIG. 6 will be described using FIG. 7. The solid line L1 in FIG. 7 illustrates the zoom by arm control, while the dashed line L2 illustrates the operation of the zoom (optical zoom and/or electronic zoom) by the camera head 3103.

The left side of the vertical axis is an axis illustrating the magnification of the zoom by the camera head 3103, and is the axis with respect to the solid line L1. The right side of the vertical axis is an axis illustrating the working distance (WD), which is the distance from the front end of the lens of the lens tube 3101 to the subject, and is the axis with respect to the dashed line L2.

Figure 7:
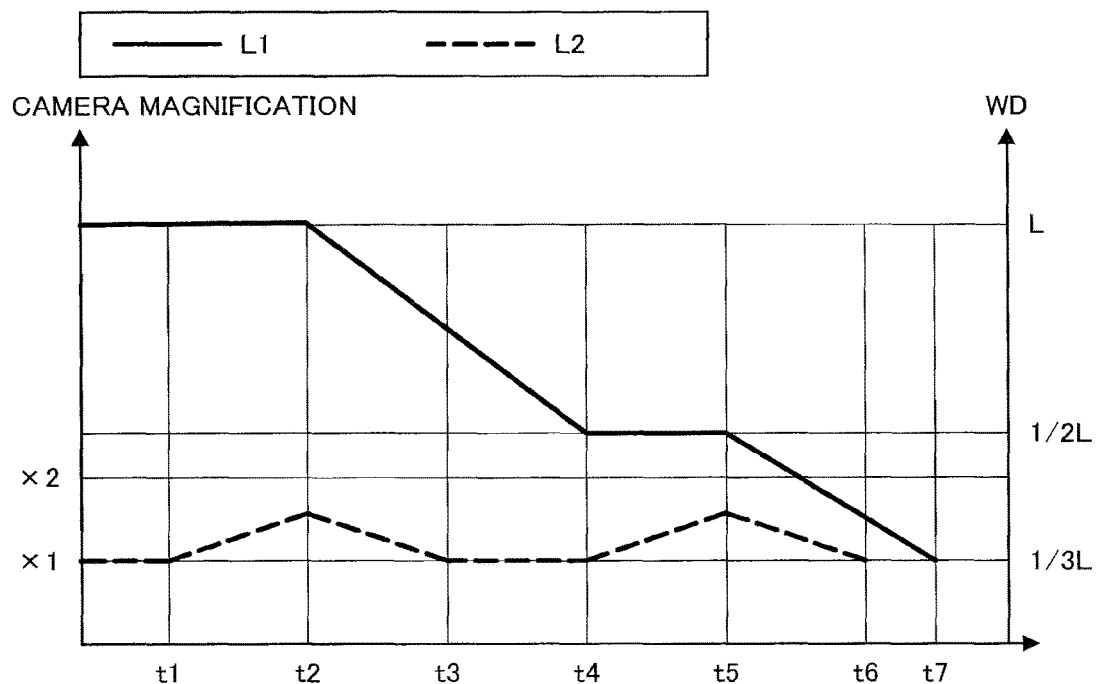
FIG. 7 is a diagram illustrating transitions in the zoom operation by arm control illustrated in FIG. 6.

In FIG. 7, the initial value of the magnification of the zoom by the camera head 3103 is ×1, and the initial value of the WD is L. Note that the following description assumes that ×2 is the limit value of the magnification by the camera head 3103.

When the user gives a zoom instruction at t1, the zoom by the camera head 3103 is executed before the zoom by arm control. The reason for executing the zoom by the camera head 3103 before the zoom by arm control in this way is because the zoom operation by the camera head 3103 is faster than the zoom operation by arm control.

Also, since it takes time for the arm section 3303 to start moving in the zoom operation by arm control, it is preferable for the zoom operation by the camera head 3103 to be executed ahead of the zoom operation by arm control.

Next, at t2, when the zoom magnification by the camera head 3103 reaches a predetermined value smaller than the limit value of ×2, the zoom magnification by the camera head 3103 starts to fall. Lowering the zoom magnification by the camera head 3103 before the limit value is reached in this way leaves room to accommodate a sudden zoom operation request from the user. For example, the zoom magnification can be returned to a magnification of ×1 rapidly in response to a user instruction, and the surgeon 3501 can be accommodated immediately when the surgeon 3501 wants to see an overhead image of the operating site. Also, by not using the electronic zoom up to the limit magnification, image quality degradation is reduced.

Also, at t2, when the zoom magnification by the camera head 3103 reaches a predetermined value smaller than the limit value of ×2, the zoom by arm control is started. The zoom by arm control is performed by having the arm section 3303 move to bring the lens closer to the subject. Next, at t3, the zoom by the camera head 3103 is returned to the zoom magnification of ×1. Subsequently, the zoom by arm control is executed until t4, at and t4, WD becomes ½ of the initial value. At this time, a ×2 magnification of the initial value is achieved by the zoom operation by arm control.

After t4, in the case of another zoom operation instruction from the user, a zoom operation similar to t1 to t4 is repeated, and at time t7, the zoom magnification becomes ×3. Similarly to time t2, at time t5 the magnification of the zoom by the camera head 3103 starts to decrease, and at time t6, the magnification of the zoom by the camera head 3103 returns to ×1. After t6, the zoom operation by arm control is continued, and at t7, the WD becomes ⅓ of the initial value by the zoom operation by arm control. By this arrangement, the distance between the lens and the subject becomes smaller, and the zoom magnification becomes ×3 of the initial value.

(Image Quality Priority Mode)

The above describes an overview of the zoom operation in the endoscopic surgery system 3000 of the present disclosure. In the following, the zoom operation in the endoscopic surgery system 3000 will be described for when a mode that prioritizes image quality has been selected by the user.

As demonstrated by Table 1 described above, the electronic zoom is inferior to the other two zoom methods in terms of image quality. Consequently, in the case in which a mode that prioritizes image quality is selected, the zoom operation is executed by prioritizing the optical zoom and the zoom operation by arm control.

Figure 8:
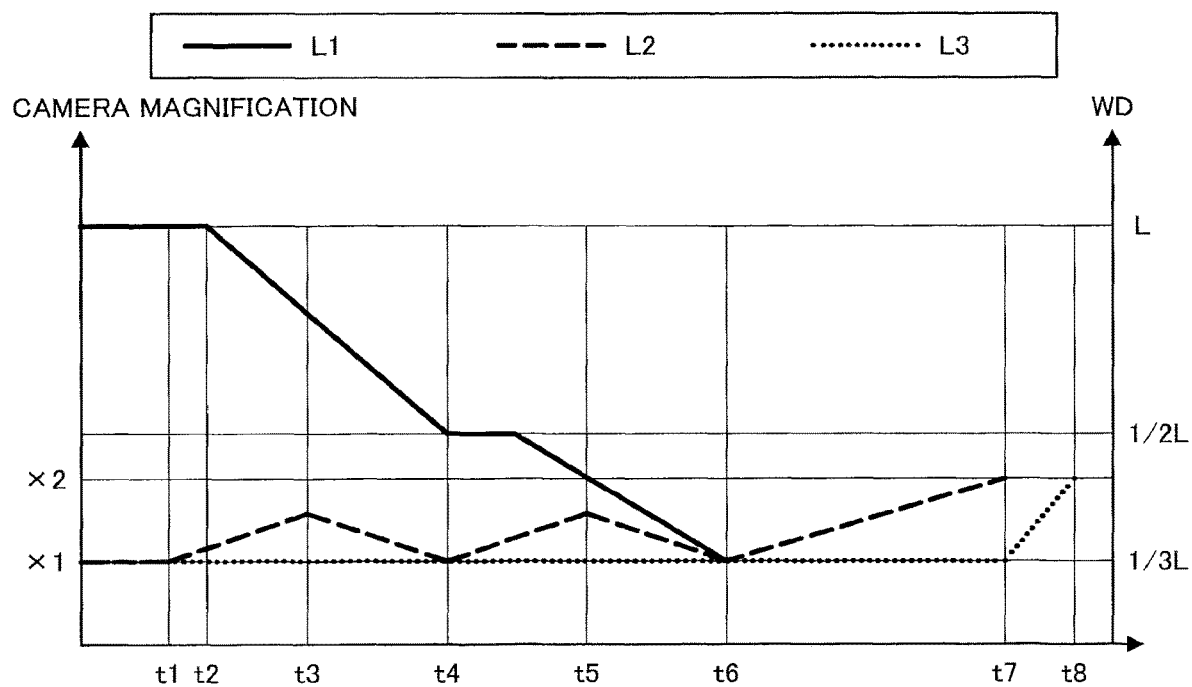
FIG. 8 is a diagram illustrating another example of transitions in the zoom operation by arm control illustrated in FIG. 6.

FIG. 8 is a diagram illustrating the relationship between each zoom operation in the case in which the image quality priority mode is selected. The solid line L1 in FIG. 8 illustrates the operation of the optical zoom, the dashed line L2 illustrates the operation of the zoom by arm control, and the dotted line L3 illustrates the operation of the zoom by electronic zoom.

The operations from t1 to t6 correspond to the zoom operation illustrated in FIG. 7. However, in the image quality priority mode, the zoom operation by the optical zoom is executed as the zoom operation by the camera head 3103 illustrated in FIG. 7. As described above using FIG. 7, at time t6, the magnification becomes ×3 of the initial value.

If the user gives a zoom instruction after time t6, the optical zoom is executed ahead of the electronic zoom. Subsequently, at t7, when the optical zoom is executed up to the limit value, the magnification becomes ×6 of the initial value. If the user gives a zoom instruction after t7, the electronic zoom is finally executed. Subsequently, at t8, when the electronic zoom is executed up to the limit value, the magnification becomes ×12 of the initial value. By executing the optical zoom and the zoom by arm control before executing the electronic zoom in this way, the image is enlarged while maintaining image quality.

The above describes the zoom operation in the case in which the mode that prioritizes image quality is selected. In the following, the operation will be described for the case in which a mode that prioritizes the speed of zooming has been selected. As Table 1 demonstrates, regarding the response speed as a zoom operation, the electronic zoom is the fastest, and the optical zoom is the next-fastest. In this way, the zoom operation by arm control is inferior to the zoom operations by the other two methods in terms of the response speed of the zoom operation.

(Speed Priority Mode)

Figure 9:
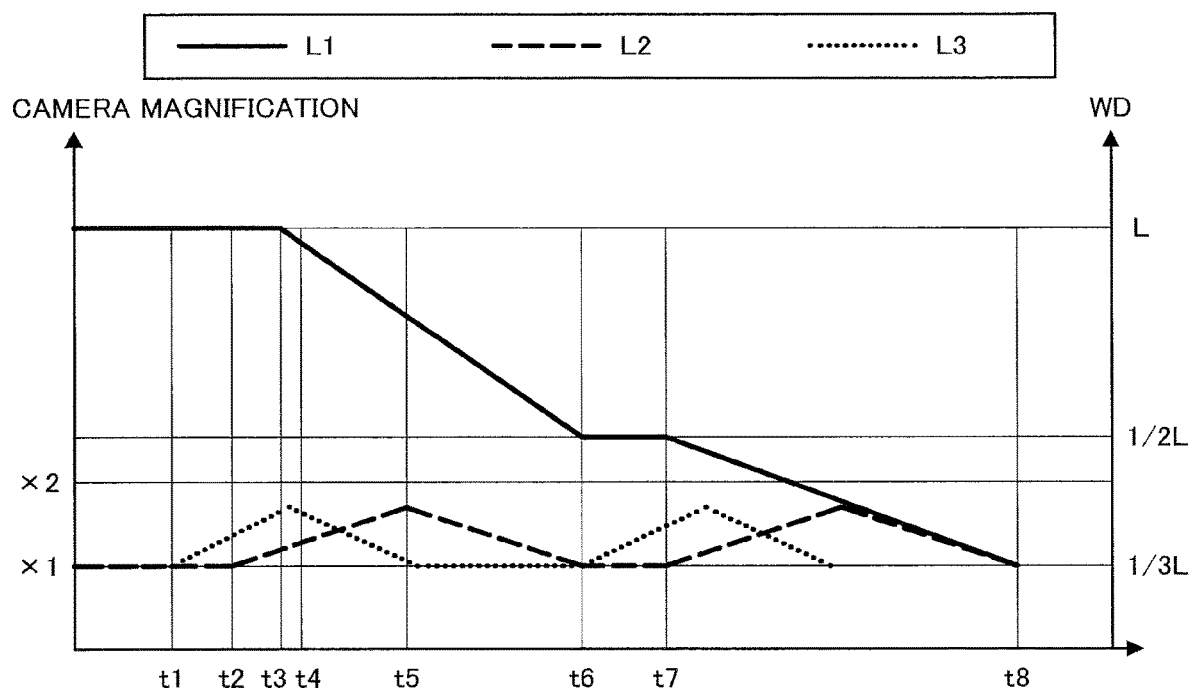
FIG. 9 is a diagram illustrating another example of transitions in the zoom operation by arm control illustrated in FIG. 6.

FIG. 9 is a diagram illustrating the relationship between each zoom operation in the case in which the speed priority mode is selected. The correspondence relationships between the dotted lines in FIG. 9 as similar to FIG. 8, in which the solid line L1 illustrates the operation of the optical zoom, the dashed line L2 illustrates the operation of the zoom by arm control, and the dotted line L3 illustrates the operation of the zoom by electronic zoom.

In the speed priority mode, at t1, the electronic zoom having the fastest response speed is executed. Next, at t2, the optical zoom having the next-fastest response speed after the electronic zoom is executed. Subsequently, at t3, the zoom by arm control is executed before the magnification of the electronic zoom reaches the limit value of ×2. Subsequently, at time t4, the magnification becomes ×2 of the initial value by the three of the electronic zoom, the optical zoom, and the zoom by arm control.

From t4 to t5, the zoom magnification by the electronic zoom decreases while the optical zoom and the zoom by arm control continue to be executed. At time t5, the zoom magnification by optical zoom begins to decrease while the zoom operation by arm control continues to be executed.

At time t6, the magnification of the electronic zoom and the optical zoom return to ×1. In addition, the WD from the front end of the lens to the subject becomes ½ of the initial value by arm control, and the magnification of the zoom by arm control becomes ×2. Thus, the overall zoom magnification becomes ×2.

Subsequently, from t6 to t8, similarly to t1 to t6, zoom operations are executed in the order of the electronic zoom, the optical zoom, and the zoom by arm control. Additionally, from t7 up until t8, the magnification of the electronic zoom and the optical zoom returns to ×1, and the WD becomes ⅓ of the initial value, thereby causing the magnification of the zoom by arm control to become ×3. Thus, the overall zoom magnification becomes ×3. By executing zoom operations in order of fastest response speed of the zoom operation in this way, it is possible to accommodate zoom instructions from the user quickly. Also, by executing the electronic zoom and the optical zoom before the zoom operation by arm control, time for moving the arm can be gained.

Note that in the endoscopic surgery system 3000, the position of a portion of the arm section 3303, or the position of the endoscope 3100 attached to the arm front end may be fixed by a trocar or the like in some cases. Also, even with a surgical microscope or the like, in some cases it may be desirable to impose restrictions on the motion of the arm from the perspective of securing the field of view for the surgeon or securing a surgical area. In the case of such a mode, the zoom operations in the endoscopic surgery system 3000 of the present disclosure are executing by prioritizing the optical zoom or the electronic zoom by the camera head 3103 over the zoom operation by arm control. With this arrangement, the position of the arm is controlled not to change as much as possible.

(Summary of Second Embodiment)

In the endoscopic surgery system 3000 of the present disclosure as described above, in addition to the zoom (electronic zoom and optical zoom) by the camera head 3103, the zoom operation by arm control is executed, thereby making it possible to zoom up to a magnification that cannot be accommodated with only the zooming by the camera head 3103. Thus, the display image can be enlarged or reduced to the magnification desired by the surgeon 3501 or an assistant.

Also, by providing an image quality priority mode and a speed priority mode, and changing the zoom operations used depending on the selected mode, the display image can be enlarged or reduced according to the image quality or speed desired by the surgeon 3501 or an assistant.

4. Third Embodiment (Operation of Sorting Display Image Based on Type of Surgical Instrument)

The above describes an embodiment in which the zoom operation by arm control is executed in addition to the zoom (electronic zoom and optical zoom) by the camera head 3103. In the following, an operation of sorting the display image based on the type of surgical instrument 3200 will be described.

Figure 10:
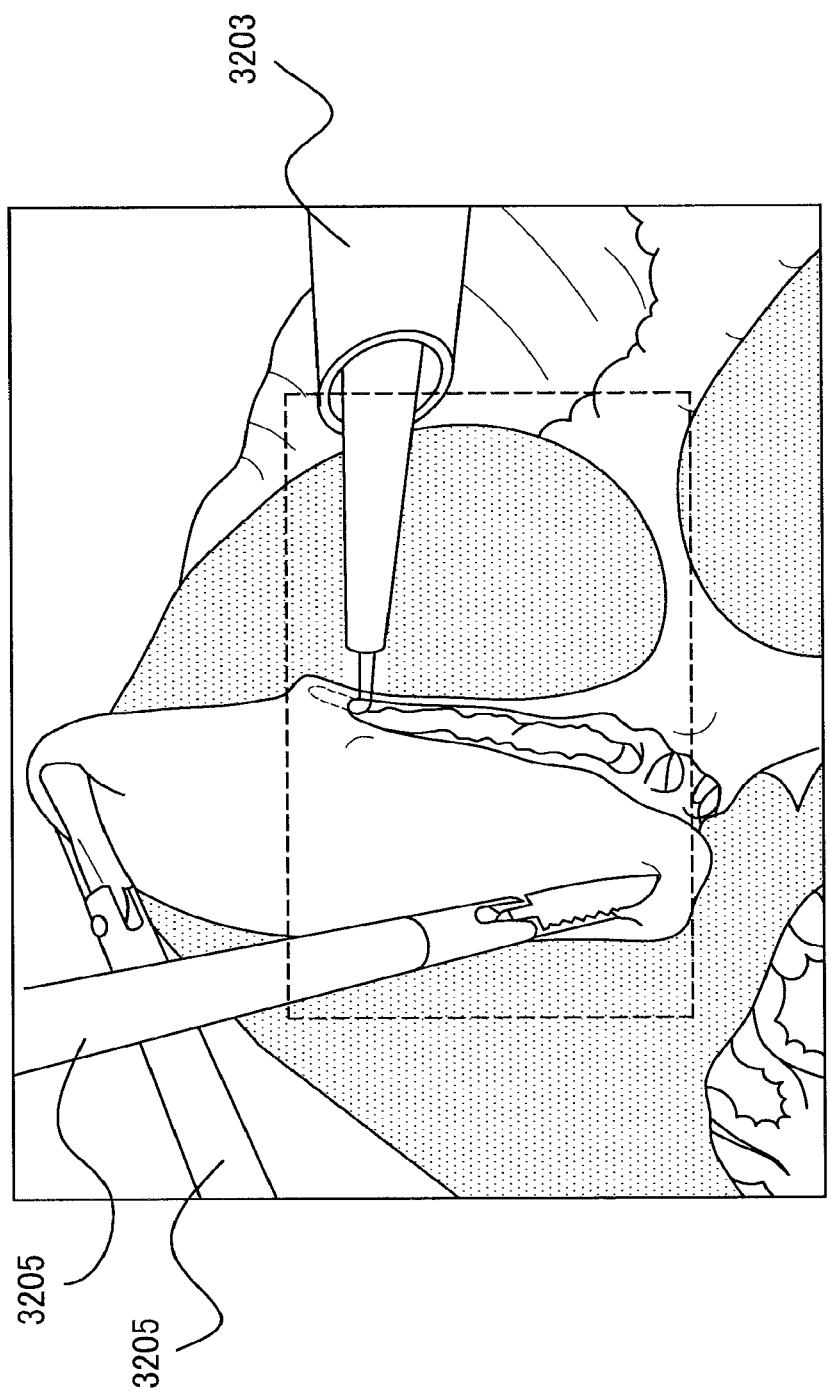
FIG. 10 is a diagram illustrating a display image sorting operation based on the type of surgical instrument in the present disclosure.

FIG. 10 is a diagram illustrating an example of a captured image of an operating site captured by the imaging section 3107. In the endoscopic surgery system 3000, various surgical instruments 3200 are used. For example, the surgeon 3501 excises an affected area using an energy treatment tool 3203, and an assistant assists the surgeon 3501 by holding the affected area using forceps 3205.

Since the treatments performed by the surgeon 3501 and the assistant are different, the fields of view desired by each are also different. For example, since the surgeon 3501 performs a minute treatment such as cutting out an affected area using the energy treatment tool 3203, the surgeon 3501 desires an enlarged image of the operating site. Meanwhile, since the assistant wants to confirm whether the surgical instruments 3200 are damaging other organs, the assistant desires an overhead image including the entirety of the surgical instruments 3200.

Consequently, the CCU 3401 outputs the region illustrated by the dashed line in FIG. 10 to a main monitor for the surgeon 3501, and outputs the region illustrated by the solid line in FIG. 10 to a sub-monitor, which is different from the main monitor, for the assistant. Herein, the region illustrated by the solid line in FIG. 10 includes three surgical instruments (one energy treatment tool 3203 and two forceps 3205), and all of the front ends of the three surgical instruments 3200 are included in the captured image illustrated by the solid line in FIG. 10. Hereinafter, all of the front ends of the surgical instruments 3200 being included means that the front ends of all surgical instruments 3200 included in the captured image are included in the captured image.

FIG. 11 is a flowchart illustrating the display image sorting operation described above. First, in S300, the CCU 3401 detects surgical instruments 3200. At this time, the CCU 3401 distinguishes whether a detected surgical instrument 3200 is a surgical instrument 3200 for use by the surgeon, or a surgical instrument 3200 for use by an assistant. Next, in S302, the CCU 3401 determines whether or not the front ends of all surgical instruments 3200 included in the captured image are included in the captured image.

In S302, if the CCU 3401 determines that all of the front ends of the surgical instruments 3200 are included inside the captured image, the process proceeds to S308. In S308, the CCU 3401 outputs an enlarged image including the surgical instrument 3200 for use by the surgeon to the main monitor, and outputs an image including all of the front ends of the surgical instruments 3200 to the sub-monitor as an overhead image for use by the assistant. Note that the enlarged image is created by cropping out a portion of the captured image and executing the electronic zoom.

In S302, if the CCU 3401 determines that not all of the front ends of the surgical instruments 3200 are included inside the captured image, the process proceeds to S304. In S304, to execute the zoom operation by arm control, the CCU 3401 sends control information for controlling the arm section 3303 to the arm control apparatus 3407. The control information sent at this time may include the movement amount or speed by which to move the arm section 3303, or information related to the positions of the surgical instruments 3200.

The arm control apparatus 3407 receives the control information in S304, and the arm control apparatus 3407 computes a movement amount of the arm section 3303, and causes the arm section 3303 to move (S306). Next, the process returns to S300, and S300 to S306 are repeated. In other words, when the arm control apparatus 3407 moves the arm section 3303, the CCU 3401 determines whether or not all of the front ends of the surgical instruments 3200 are included in the captured image. Subsequently, if not all of the front ends of the surgical instruments 3200 are included, the CCU 3401 sends control information, and the arm control apparatus 3407 moves the arm section 3303 on the basis of the control information.

A zoom out is performed by the movement of the arm section 3303 through repetition of the process from S300 to S306. Additionally, in S302, if the CCU 3401 determines that all of the front ends of the surgical instruments 3200 are included in the captured image, the CCU 3401 outputs an enlarged image including the surgical instrument 3200 of the surgeon 3501 to the main monitor (S308). Also, the CCU 3401 outputs an image including all of the front ends of the surgical instruments 3200 to the sub-monitor (S308).

Note that the detection of the surgical instruments 3200 in S300 is executed by detecting the edge shapes and/or colors of the surgical instruments 3200, the brightness gradient of the surgical instruments 3200, and the like as described above. Also, the detection of the surgical instruments 3200 may also be executed using machine learning.

Also, in the detection of the surgical instruments 3200 in S300, it is determined whether a surgical instrument 3200 is a surgical instrument 3200 used by the surgeon 3501, or a surgical instrument 3200 used by an assistant. This determination may be made by having the endoscopic surgery system 3000 store patterns of the edge shapes and/or colors of the surgical instruments 3200 and the brightness gradients of the surgical instruments 3200 described above for each of the surgical instruments 3200, and executing pattern matching. Also, since the surgical instruments 3200 such as the forceps 3205 used by the assistant basically do not move, the CCU 3401 may also detect the motion of a surgical instrument 3200, and determine that a moving surgical instrument 3200 is a surgical instrument 3200 used by the surgeon 3501.

In the example described above, the zoom position and the enlargement ratio are executed according to the detection results of the surgical instruments 3200. However, in the zoom enlargement, it is also possible to take a configuration that presents a display at not only an enlargement ratio whereby the surgical instruments 3200 are included, but also an enlargement ratio whereby both the region of the affected area and the surgical instruments 3200 are included. In this case, the specification of the region of the affected area may be based on a learning process similar to the process of detecting the surgical instruments 3200, or may be detected on the basis of a result of observation by special light (narrow-band light, fluorescence excitation light).

(Summary of Third Embodiment)

In the surgery system 3000 of the present disclosure as described above, a display image for the surgeon and a display image for the assistant can be sorted to different monitors. Consequently, it is possible to provide display images with the angle of view desired by each of the surgeon 3501 and the assistant.

5. Supplement

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, in FIG. 11, only the zoom operation by arm control is described, but the zoom operation by arm control may also be executed after the optical zoom is executed. With this arrangement, a large zoom out can be executed, and images desired by the surgeon 3501 and the assistant are provided. Also, since the optical zoom has a faster response speed than the zoom by arm control, time for moving the arm section 3303 can be gained.

6. Conclusion

According to the embodiments of the present disclosure as described above, not only imaging control by the camera head 3103 but also imaging control by arm control is executed. With this arrangement, the surgeon 3501 or an assistant is able to acquire one's desired display image.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
A medical information processing apparatus including:
an image control section that controls processing of a captured image from a camera; and
an arm control section that controls a motion of an arm section that supports the camera, in which
one of the image control section and the arm control section executes control on a basis of control information from another control section.

(2)
The medical information processing apparatus according to (1), in which
the image control section detects a treatment tool from a captured image captured by the camera, and
the image control section changes a cropping position of the captured image according to a motion of the detected treatment tool.

(3)
The medical information processing apparatus according to any one of (1) and (2), in which
the image control section sends control information to the arm control section on a basis of a motion of the detected treatment tool, and
the arm control section computes a movement amount by which to move the arm section on a basis of the control information received from the image control section.

(4)
The medical information processing apparatus according to (3), in which
the arm control section sends the computed movement amount of the arm section to the image control section, and
the image control section changes the cropping position of the captured image on a basis of the movement amount of the arm section received from the arm control section.

(5)
The medical information processing apparatus according to any one of (3) and (4), in which
in a case in which the motion of the treatment tool exceeds a predetermined standard, the image control section sends control information for controlling the arm section to the arm control section.

(6)
The medical information processing apparatus according to any one of (1) to (5), in which
the image control section sends an enlargement instruction to the camera, and
when the image control section determines that enlargement by movement of the arm section is more suitable than enlargement by the camera,
the image control section sends control information for controlling the arm section to the arm control section.

(7)
The medical information processing apparatus according to (6), in which
the enlargement by the camera includes an optical zoom and an electronic zoom, and
in a case in which a mode that prioritizes image quality is selected, the image control section controls the optical zoom prior to the electronic zoom.

(8)
The medical information processing apparatus according to (6), in which
the enlargement by the camera includes an optical zoom and an electronic zoom, and
in a case in which a mode that prioritizes a speed of enlarging an image is selected, the image control section controls the electronic zoom prior to the optical zoom.

(9)
The medical information processing apparatus according to any one of (6) to (8), in which
the image control section sends the control information to the arm control section before an enlargement magnification by the camera reaches a limit value.

(10)
The medical information processing apparatus according to any one of (1) to (9), in which
the image control section detects a plurality of treatment tools from a captured image captured by the camera, and
the image control section executes a reduction process such that front ends of the detected plurality of treatment tools are all included in the captured image.

(11)
The medical information processing apparatus according to (10), in which
the image control section additionally detects types of the treatment tools, and
the image control section crops the captured image such that a treatment tool for use by a surgeon is included in a display image.

(12)
An information processing method including:
controlling processing of a captured image from a camera; and
controlling a motion of an arm section that supports the camera, in which
one of the control of the processing of the captured image and the control of the motion of the arm section executes control on a basis of on control information from other control.

(13)

A medical information processing system including:
a camera that captures an image;
an image control section that controls processing of a captured image from the camera;
an arm section that supports the camera; and
an arm control section that controls a motion of the arm section that supports the camera, in which
one of the image control section and the arm control section executes control on a basis of control information from another control section.

REFERENCE SIGNS LIST 3000 endoscopic surgery system
3100 endoscope
3101 lens tube
3103 camera head
3105 lens unit
3107 imaging section
3109 driving section
3111 communication section
3113 camera head control section
3200 surgical instrument
3201 pneumoperitoneum tube
3203 energy treatment tool
3205 forceps
3300 support arm apparatus
3301 base section
3303 arm section
3400 cart
3401 camera control unit (CCU)
3403 display apparatus
3405 light source apparatus
3407 arm control apparatus
3409 input apparatus
3411 treatment tool control apparatus
3413 pneumoperitoneum apparatus
3423 image processing section
3425 control section
3427 transmission cable
3501 surgeon
3503 patient bed
3505 patient

The invention claimed is:

1. A medical information processing apparatus comprising:
image control circuitry configured to control processing of a captured image from a camera; and
arm control circuitry configured to control a motion of an arm that supports the camera, wherein
one of the image control circuitry and the arm control circuitry executes control on a basis of control information from another control circuitry, and
on condition that a first mode that prioritizes image quality is selected, the image control circuitry is configured to control an optical zoom and to send control information for controlling the arm to the arm control circuitry prior to the image control circuitry being configured to control an electronic zoom, or
on condition that a second mode that prioritizes speed is selected, the image control circuitry is configured to control the electronic zoom prior to the optical zoom, wherein the electronic zoom decreases as the optical zoom increases so that the electronic zoom is replaced by the optical zoom in the second mode.

2. The medical information processing apparatus according to claim 1, wherein
the image control circuitry is configured to detect a treatment tool from a captured image captured by the camera, and
the image control circuitry is configured to change a cropping position of the captured image according to a motion of the detected treatment tool.

3. The medical information processing apparatus according to claim 2, wherein
the image control circuitry sends control information to the arm control circuitry on a basis of a motion of the detected treatment tool, and
the arm control circuitry computes a movement amount by which to move the arm on a basis of the control information received from the image control circuitry.

4. The medical information processing apparatus according to claim 3, wherein
the arm control circuitry is configured to send the computed movement amount of the arm to the image control circuitry, and
the image control circuitry changes the cropping position of the captured image on a basis of the movement amount of the arm received from the arm control circuitry.

5. The medical information processing apparatus according to claim 3, wherein
in a case in which the motion of the treatment tool exceeds a predetermined standard, the image control circuitry sends control information for controlling the arm to the arm control circuitry.

6. The medical information processing apparatus according to claim 1, wherein
the image control circuitry is configured to send an enlargement instruction to the camera, and
enlargement by the camera includes the optical zoom and enlargement by the image control circuitry and/or the camera includes the electronic zoom.

7. The medical information processing apparatus according to claim 1, wherein, in the second mode,
the image control circuitry is configured to send the control information to the arm control circuitry before an enlargement magnification by the camera reaches a limit value.

8. The medical information processing apparatus according to claim 1, wherein
the image control circuitry is configured to detect a plurality of treatment tools from a captured image captured by the camera, and
the image control circuitry is configured to send the control information to the arm control circuitry such that front ends of the detected plurality of treatment tools are all included in the captured image.

9. The medical information processing apparatus according to claim 8, wherein
the image control circuitry is further configured to detect types of the treatment tools, and
the image control circuitry is configured to crop the captured image such that a treatment tool for use by a surgeon is included in a display image.

10. An information processing method comprising:
controlling processing of a captured image from a camera; and
controlling a motion of an arm that supports the camera, wherein one of the controlling of the processing of the captured image and the controlling of the motion of the arm executes control on a basis of on control information from other control, and on condition that a first mode that prioritizes image quality is selected, controlling an optical zoom and sending control information for controlling the arm to arm control circuitry prior to controlling an electronic zoom, or on condition that a second mode that prioritizes speed is selected, controlling the electronic zoom prior to the optical ZOOM, wherein the electronic zoom decreases as the optical zoom increases so that the electronic zoom is replaced by the optical zoom in the second mode.

11. A medical information processing system comprising:
a camera that captures an image;
an image control circuitry configured to control processing of a captured image from the camera;
an arm that supports the camera; and
an arm control circuitry configured to control a motion of the arm that supports the camera, wherein
one of the image control circuitry and the arm control circuitry executes control on a basis of control information from another control circuitry, and
on condition that a first mode that prioritizes image quality is selected, the image control circuitry is configured to control an optical zoom and to send control information for controlling the arm to the arm control circuitry prior to the image control circuitry being configured to control an electronic zoom, or
on condition that a second mode that prioritizes speed is selected, the image control circuitry is configured to control the electronic zoom prior to the optical zoom, wherein the electronic zoom decreases as the optical zoom increases so that the electronic zoom is replaced by the optical zoom in the second mode.

12. The information processing method according to claim 10, wherein, in the second mode,
sending the control information for controlling the motion of the arm before an enlargement magnification by the camera reaches a limit value.

13. The information processing method according to claim 10, further comprising sending an enlargement instruction to the camera, enlargement by the camera including the optical zoom, wherein enlargement by the electronic zoom includes controlling processing of the captured image and/or the camera.

14. The medical information processing system according to claim 11, wherein, in the second mode,
the image control circuitry is configured to send the control information to the arm control circuitry before an enlargement magnification by the camera reaches a limit value.

15. The medical information processing system according to claim 11, wherein
the image control circuitry is configured to send an enlargement instruction to the camera, and
enlargement by the camera includes an optical zoom and enlargement by the image control circuitry and/or the camera includes an electronic zoom.

16. The medical information processing system according to claim 11, wherein the camera is one of an endoscope and a microscope that captures an image of a site for a medical procedure.

* * * * *